United States Patent
Dave et al.

(10) Patent No.: US 10,207,489 B2
(45) Date of Patent: Feb. 19, 2019

(54) SYSTEMS AND METHODS FOR ADDITIVE MANUFACTURING OPERATIONS

(71) Applicant: SIGMA LABS, INC., Santa Fe, NM (US)

(72) Inventors: Vivek R. Dave, Concord, NH (US); Mark J. Cola, Santa Fe, NM (US); R. Bruce Madigan, Butte, MT (US); Alberto Castro, Santa Fe, NM (US); Glenn Wikle, Santa Fe, NM (US); Lars Jacquemetton, Santa Fe, NM (US); Peter Campbell, Albuquerque, NM (US)

(73) Assignee: SIGMA LABS, INC., Santa Fe, NM (US)

( * ) Notice: Subject to any disclaimer, the term of this patent is extended or adjusted under 35 U.S.C. 154(b) by 263 days.

(21) Appl. No.: 15/282,822

(22) Filed: Sep. 30, 2016

(65) Prior Publication Data
US 2017/0090462 A1 Mar. 30, 2017

Related U.S. Application Data

(60) Provisional application No. 62/235,232, filed on Sep. 30, 2015.

(51) Int. Cl.
*G06F 19/00* (2018.01)
*B33Y 30/00* (2015.01)
(Continued)

(52) U.S. Cl.
CPC ............... *B33Y 30/00* (2014.12); *B33Y 50/00* (2014.12); *G01N 21/00* (2013.01); *G01N 21/71* (2013.01);
(Continued)

(58) Field of Classification Search
CPC ......... B33Y 30/00; B33Y 50/00; H01L 22/12; G01N 21/00; G01N 21/71; G01N 2021/8411; G06N 99/005
See application file for complete search history.

(56) References Cited

U.S. PATENT DOCUMENTS

| 3,499,310 A | 3/1970 | Hundere et al. |
| 4,041,476 A | 8/1977 | Swainson et al. |

(Continued)

FOREIGN PATENT DOCUMENTS

| CN | 107428081 A | 12/2017 |
| DE | 102013206542 A1 | 10/2014 |

(Continued)

OTHER PUBLICATIONS

Dunsky, "Process Monitoring in Laser Additive Manufacturing", Industrial Laser Solutions for Manufacturing, Sep. 12, 2014, 9 pages.

(Continued)

*Primary Examiner* — Adam Lee
(74) *Attorney, Agent, or Firm* — Kilpatrick Townsend & Stockton LLP

(57) ABSTRACT

This disclosure describes various system and methods for monitoring photons emitted by a heat source of an additive manufacturing device. Sensor data recorded while monitoring the photons can be used to predict metallurgical, mechanical and geometrical properties of a part produced during an additive manufacturing operation. In some embodiments, a test pattern can be used to calibrate an additive manufacturing device.

20 Claims, 17 Drawing Sheets

(51) Int. Cl.
| | |
|---|---|
| *B33Y 50/00* | (2015.01) |
| *G01N 21/00* | (2006.01) |
| *G01N 21/71* | (2006.01) |
| *H01L 21/66* | (2006.01) |
| *G06N 99/00* | (2010.01) |
| *G01N 21/84* | (2006.01) |

(52) U.S. Cl.
CPC ...... *H01L 22/12* (2013.01); *G01N 2021/8411* (2013.01); *G06N 99/005* (2013.01)

(56) References Cited

U.S. PATENT DOCUMENTS

| | | |
|---|---|---|
| 4,247,508 A | 1/1981 | Housholder et al. |
| 4,323,756 A | 4/1982 | Brown et al. |
| 4,575,330 A | 3/1986 | Hull |
| 4,863,538 A | 9/1989 | Deckard |
| 5,272,027 A | 12/1993 | Dillenbeck et al. |
| 5,962,065 A | 10/1999 | Weimer et al. |
| 6,261,493 B1 | 7/2001 | Gaylo et al. |
| 6,357,910 B1 | 3/2002 | Chen et al. |
| 6,483,596 B1 | 11/2002 | Philippi et al. |
| 6,547,994 B1 | 4/2003 | Monkhouse et al. |
| 6,554,600 B1 | 4/2003 | Hofmann et al. |
| 6,672,343 B1 | 1/2004 | Perret et al. |
| 6,824,714 B1 | 11/2004 | Türck et al. |
| 6,930,278 B1 | 8/2005 | Chung et al. |
| 6,932,935 B1 | 8/2005 | Oberhofer et al. |
| 7,127,304 B1 | 10/2006 | Gould et al. |
| 7,153,463 B2 | 12/2006 | Leuterer et al. |
| 7,229,272 B2 | 6/2007 | Leuterer et al. |
| 7,419,632 B2 | 9/2008 | Keller et al. |
| 7,601,422 B2 | 10/2009 | Mueller et al. |
| 7,628,600 B2 | 12/2009 | Perret et al. |
| 7,661,948 B2 | 2/2010 | Perret et al. |
| 7,665,979 B2 | 2/2010 | Heugel et al. |
| 7,674,107 B2 | 3/2010 | Perret et al. |
| 7,686,605 B2 | 3/2010 | Perret et al. |
| 7,713,048 B2 | 5/2010 | Perret et al. |
| 7,740,683 B2 | 6/2010 | Thorsson et al. |
| 7,820,241 B2 | 10/2010 | Perret et al. |
| 7,837,458 B2 | 11/2010 | Perret et al. |
| 7,847,057 B2 | 12/2010 | Mueller et al. |
| 7,850,885 B2 | 12/2010 | Philippi et al. |
| 7,891,095 B2 | 2/2011 | Thorsson et al. |
| 7,901,604 B2 | 3/2011 | Oberhofer et al. |
| 7,931,462 B2 | 4/2011 | Mattes et al. |
| 7,946,840 B2 | 5/2011 | Perret et al. |
| 7,976,302 B2 | 7/2011 | Perret et al. |
| 8,031,384 B2 | 10/2011 | Schimitzek et al. |
| 8,034,279 B2 | 10/2011 | Dimter et al. |
| 8,073,315 B2 | 12/2011 | Philippi et al. |
| 8,075,814 B2 | 12/2011 | Fruth et al. |
| 8,083,513 B2 | 12/2011 | Montero-Escuder et al. |
| 8,124,192 B2 | 2/2012 | Paasche et al. |
| 8,137,739 B2 | 3/2012 | Philippi et al. |
| 8,172,562 B2 | 5/2012 | Mattes et al. |
| 8,186,990 B2 | 5/2012 | Perret et al. |
| 8,260,447 B2 | 9/2012 | Mattes et al. |
| 8,299,208 B2 | 10/2012 | Mueller et al. |
| 8,303,886 B2 | 11/2012 | Philippi et al. |
| 8,313,087 B2 | 11/2012 | Hesse et al. |
| 8,317,508 B2 | 11/2012 | Bokodi et al. |
| 8,366,432 B2 | 2/2013 | Perret et al. |
| 8,414,281 B2 | 4/2013 | Schleiss et al. |
| 8,420,001 B2 | 4/2013 | Leuterer et al. |
| 8,501,075 B2 | 8/2013 | Philippi et al. |
| 8,525,071 B2 | 9/2013 | Leuterer et al. |
| 8,658,078 B2 | 2/2014 | Weidinger et al. |
| 8,710,144 B2 | 4/2014 | Weiss et al. |
| 8,734,694 B2 | 5/2014 | Perret et al. |
| 8,784,720 B2 | 7/2014 | Göbner et al. |
| 8,784,721 B2 | 7/2014 | Philippi et al. |
| 8,803,073 B2 | 8/2014 | Philippi et al. |
| 9,925,715 B2 | 3/2018 | Cheverton et al. |
| 2008/0127186 A1 | 5/2008 | Kanodia et al. |
| 2008/0262659 A1 | 10/2008 | Huskamp et al. |
| 2009/0206065 A1 | 8/2009 | Kruth et al. |
| 2009/0312851 A1 | 12/2009 | Mishra |
| 2010/0161102 A1 | 6/2010 | Mattes et al. |
| 2011/0046766 A1 | 2/2011 | Mienhardt et al. |
| 2011/0196525 A1 | 8/2011 | Bogue |
| 2013/0083324 A1 | 4/2013 | Wilhelm |
| 2013/0114082 A1 | 5/2013 | Sailor et al. |
| 2014/0004626 A1 | 1/2014 | Ku et al. |
| 2014/0039662 A1 | 2/2014 | Boyer et al. |
| 2014/0265046 A1 | 9/2014 | Burris et al. |
| 2015/0061170 A1 | 3/2015 | Engel et al. |
| 2015/0104802 A1 | 4/2015 | Reep et al. |
| 2015/0147424 A1* | 5/2015 | Bibas ................. B29C 67/0088 425/150 |
| 2015/0177158 A1* | 6/2015 | Cheverton ......... G01N 15/0227 700/119 |
| 2015/0261196 A1* | 9/2015 | Wilson .................. B33Y 10/00 700/119 |
| 2015/0375456 A1 | 12/2015 | Cheverton et al. |
| 2016/0098825 A1* | 4/2016 | Dave ....................... G06K 9/52 419/53 |
| 2016/0176114 A1* | 6/2016 | Tsai ..................... B29C 64/386 700/98 |
| 2016/0184893 A1 | 6/2016 | Dave et al. |
| 2016/0185048 A1 | 6/2016 | Dave et al. |
| 2016/0193696 A1 | 7/2016 | McFarland et al. |
| 2016/0199911 A1 | 7/2016 | Dave et al. |
| 2016/0236279 A1* | 8/2016 | Ashton ................ B22F 3/1055 |
| 2016/0332381 A1 | 11/2016 | Long et al. |
| 2018/0036949 A1* | 2/2018 | Lopez .................... B33Y 30/00 |
| 2018/0104896 A1* | 4/2018 | Lopez .................... B29C 64/20 |

FOREIGN PATENT DOCUMENTS

| | | |
|---|---|---|
| EP | 1466718 A2 | 10/2004 |
| EP | 1700686 A2 | 9/2006 |
| EP | 2918395 A1 | 9/2015 |
| EP | 3200973 A1 | 8/2017 |
| EP | 3221076 | 9/2017 |
| EP | 3245045 | 11/2017 |
| WO | 2013021173 A1 | 2/2013 |
| WO | 2013044047 A1 | 3/2013 |
| WO | 2013128416 A2 | 9/2013 |
| WO | 2013159811 A1 | 10/2013 |
| WO | 2014144255 A2 | 9/2014 |
| WO | 2014159758 A1 | 10/2014 |
| WO | 2016081651 | 5/2016 |
| WO | 2016115284 | 7/2016 |

OTHER PUBLICATIONS

Gasteuil, et al., "Lagrangian temperature, velocity, and local heat flux measurement in Rayleigh-Benard aonvection", Physical review letters 99.23, 2007, pp. 1-4.

Hamilton, et al., "Radiant-interchange configuration factors", NASA TN2836, Dec. 1, 1952, 111 pages.

Kandula, et al., "On the Effective Therman conductivity of porous packed Beds with uniform Shperical particles", Journal of Porous Media, 2011, pp. 919-926.

Korner, et al., "Fundamental consolidation mechanisms during selective beam melting of powders", Modeling and Simulation in Materials Science and Engineering, Nov. 8, 2013, 18 pages.

PCT/US2015/061420, "International Search Report and Written Opinion", Feb. 4, 2016, 10 pages.

PCT/US2016/013303, "International Search Report and Written Opinion", dated Mar. 29, 2016, 12 pages.

"IBM Technical Disclosure Bulletin", vol. 29, Issue 11, Apr. 1, 1987, pp. 4870-4872.

Bloembergen, et al., "A New Approach to the Determination of the Liquidus and Solidus Points Associated with the Melting Curve of the Eutectic Co—C, Taking Into Account the Thermal Inertia of the Furnace", Metrologia, vol. 50, No. 3, 2013.

PCT/US2016/013303, "International Preliminary Report on Patentability", Jul. 27, 2017, 10 pages.

(56) References Cited

OTHER PUBLICATIONS

U.S. Appl. No. 14/995,183, "Notice of Allowance", dated Nov. 14, 2018, 14 pages.
EP16737843.9, "Extended European Search Report", dated Sep. 28, 2018, 13 pages.

* cited by examiner

Standard Hatch

1000

Stripes with Checkerboard

1001

Random Checkerboard

1002

1300

| Layer #s | % Variation | Power (W) | Speed (mm/s) | Distance (mm) | GED (J/mm²) |
|---|---|---|---|---|---|
| 0-150 | 0 | 195 | 1200 | 0.09 | 1.81 |
| 150-225 | -55 | 88 | 1200 | 0.09 | 0.81 |
| 225-300 | -45 | 107 | 1200 | 0.09 | 0.99 |
| 300-375 | -35 | 127 | 1200 | 0.09 | 1.17 |
| 375-450 | -25 | 146 | 1200 | 0.09 | 1.35 |
| 450-525 | -15 | 166 | 1200 | 0.09 | 1.53 |
| 525-675 | 0 | 195 | 1200 | 0.09 | 1.81 |
| 675-750 | 15 | 224 | 1200 | 0.09 | 2.08 |
| 750-825 | 25 | 244 | 1200 | 0.09 | 2.26 |
| 825-900 | 35 | 263 | 1200 | 0.09 | 2.44 |
| 900-975 | 45 | 283 | 1200 | 0.09 | 2.62 |

SYSTEMS AND METHODS FOR ADDITIVE MANUFACTURING OPERATIONS

BACKGROUND OF THE INVENTION

Additive manufacturing, or the sequential assembly or construction of a part through the combination of material addition and applied energy, takes on many forms and currently exists in many specific implementations and embodiments. Additive manufacturing can be carried out by using any of a number of various processes that involve the formation of a three dimensional part of virtually any shape. The various processes have in common the sintering, curing or melting of liquid, powdered or granular raw material, layer by layer using ultraviolet light, high powered laser, or electron beam, respectively. Unfortunately, established processes for determining a quality of a resulting part manufactured in this way are limited. Conventional quality assurance testing generally involves post-process measurements of mechanical, geometrical, or metallurgical properties of the part, which frequently results in destruction of the part. While destructive testing is an accepted way of validating a part's quality, as it allows for close scrutiny of various internal features of the part, such tests cannot for obvious reasons be applied to a production part. Consequently, ways of non-destructively and accurately verifying the mechanical, geometrical and metallurgical properties of a production part produced by additive manufacturing are desired.

SUMMARY OF THE INVENTION

An overall object of this invention is to apply optical sensing techniques to additive manufacturing processes involving the addition of thermal energy with a scanning heat source for the purpose of quality inference, process control, or both. Optical sensors can be used to track the evolution of in-process physical phenomena by tracking the evolution of their associated in-process physical variables. Herein optical can include that portion of the electromagnetic spectrum which include near infrared and well as near ultraviolet. Generally, the optical spectrum is considered to go from 380 nm to 740 nm in terms of wavelength. However near UV and near IR could extend as low as 1 nm and as high as 1000 nm in terms of wavelength respectively.

Another object of this invention to enable an optical sensing system to identify, examine, and analyze features associated with a heat source from two different process conditions and determine if they are largely similar or very different. The optical sensing system can be used to identify, examine, and analyze features associated with the material response to a heat input associated with two different process conditions to determine if they are largely similar or very different. The optical sensors can be used to interrogate a wide range of properties of the process including but not limited to in-process physical behaviors that will impact the metallurgical integrity, the mechanical properties, or the geometric shape of the article thus manufactured.

It is a further object of this invention to enable an optical sensing process together with suitable feature extraction to discern and distinguish various process conditions based on their associated characteristic times, for example, to the extent that the characteristic times and other dimensional or dimensionless parameters delineate different regimes of behavior, the optical sensing system and associated feature extraction methods will have sufficient resolution and accuracy to distinguish these same regimes of behavior.

Another object of this invention is to determine if process features from the slower material response to the heat input and associated with a given process condition are largely similar to those associated with a known baseline process condition and therefore considered nominal or very different from that baseline condition and therefore considered off-nominal.

It is a further object of this invention to derive process features from these thermal data gathered on these two very different timescales.

It is still a further object of this invention to apply such optical sensing and feature extraction methodologies to instances in which there are multiple beams, or where a single beam has been divided into several heat sources.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION OF THE INVENTION

Figure 1:
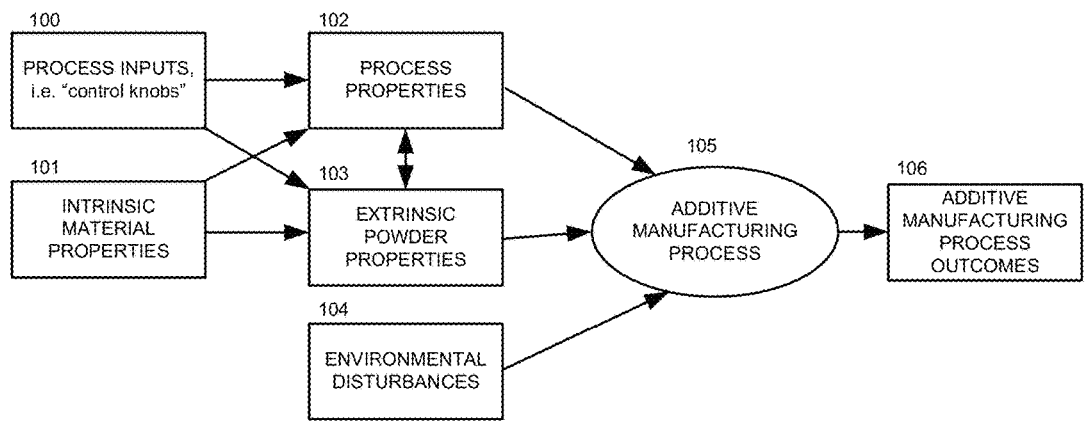
FIGS. 1-5 show flow charts describing methods and properties associated with the described embodiments.

It should be first recognized that additive manufacturing is directly dependent on three sets of properties. These properties are interrelated and they interact in a highly non-linear manner to either result in an acceptable part with acceptable metallurgical and geometric properties, or alternatively result in a part which is deficient in some manner with respect to metallurgical properties, geometric properties, or some combination of both. These specific three sets of properties are now delineated: (1) INTRINSIC MATERIAL PROPERTIES. These are the properties of the alloy that comprises the powders being used in the additive manufacturing process. Examples of such properties include melting range, vaporization range, specific heat, thermal conductivity, density, composition, latent heats of melting and vaporization, etc.; (2) EXTRINSIC POWDER BED PROPERTIES. Although the alloy has its own intrinsic properties as outlined above, the powder bed will have additional extrinsic properties which could vary from run to run or from one batch of powder to another, even if the alloy composition and all other intrinsic properties are identical. Examples of such extrinsic properties include particle size distribution, particle shape and morphology, particle surface area, particle contamination and thickness of oxide layer, packing density/powder bed density, etc.; and (3) PROCESS PROPERTIES. These are the myriad of properties that characterize the physical manufacturing process irrespective of intrinsic alloy properties and extrinsic powder properties. Examples of these properties include spatial beam power distribution, beam spot size, temporal variations in the beam if any, the environment in the processing chamber (gas or vacuum), beam travel speed and scan strategy of the beam rastering, properties of the beam optics (optical or magnetic/ electrostatic), the method for application of sequential layers of powder, also known as recoating, the preheat of the powder bed if any, the macro level cooling and heat sinking to remove thermal energy from the processing chamber, etc.

It should be noted that there are critical in-process physical behaviors which occur during the additive manufacturing process which together with the three sets of properties listed above determine elements of the outcome of the process. These categories of physical behaviors may be separated into behaviors occurring on-heating and on-cooling.

For material heating, the various physical mechanisms or behaviors involved include: (1) Physics and attributes of beam and process conditions including: beam size, spatial beam power distribution (Gaussian, tophat, etc), temporal beam power distribution (continuous, pulsed, modulated, etc), and translational velocity of beam with respect to material; (2) Beam-material interaction including: Preheating, done intentionally as is the case of electron beam or occurs dynamically as the beam moves over the powder bed and material directly in front of the beam heats and expands before the beam actually gets there due to thermal conduction "wave" in front of beam, But for most cases of interest, the moving heat source in additive manufacturing is "supersonic" with respect to the heat conduction time, i.e. the heat source is moving faster than the speed of heat conduction, Absorption of energy at an atomistic level, For photons energy absorption depends on micro and macro optical properties of the material such as reflectivity and absorptivity, as well as non-imaging concentration effects due to the surface irregularities of the powder bed, as well as interactions between the incoming photons and the vapor or plasma generated by previous heating events, For electrons, the energy absorption depends on the atomic number of the material absorbing the energy, its density, and the kinetic energy of the incident electrons;

(3) Rapid heating and melting involving: The powders thus irradiated are rapidly heated and they undergo phase transformation as they melt, Particle size distribution dictates rates which the top surface particles vaporize, Unmelted or small droplets of melted material could be ejected as well from the irradiated region—this is extensively observed in practice, and Melting will most likely occur at local, incipient sites such as tops of particles, in the crevices between particles where photons get optically concentrated through non-imaging concentration, etc.; (4) Material consolidation—a very complex phenomenon which depends on many factors including: Layer thickness of material to be consolidated—the amount of material to be consolidated vs. the amount of joules deposited by the moving heat source during the beam interaction time; Particle size distribution, which can be used to determine both thermal conductivity of the powder bed as well as the possible occurrence of porosity; Packing density—this physical attribute determines the thermal conductivity of the power bed; Surface energy characteristics and wetting of unmelted powders below the weld pool by incipient liquid; Capillary forces—this is mainly characterized by the interplay between surface tension and viscosity; Rayleigh-type consolidation mechanisms, i.e. assuming a low viscosity fluid, looking only at the interplay of inertial and surface tension effects to restore equilibrium liquid shape/consolidate particles; and Larger scale hydrodynamic forces—if a fully developed weld pool emerges then there could be several forces that could come into play including inertial, surface tension, and temperature coefficient of surface tension (Marangoni effects); (5) On-cooling physical behaviors could include the following: rapid solidification—generally the solidification behavior of melts in an AM process will be very fast and will not necessarily follow the phase equilibria as outlined in an equilibrium phase diagram. In other words, the contour lines delineating phase boundaries such as the liquidus or solidus lines could have different locations in a temperature vs. composition space, for example, Residual stress—any time when there is a non-linear cooling profile as there will be in the case of additive manufacturing, there will arise thermal stresses. As the material cools and the strength of the material gradually increases, some of these thermal stresses could be "locked in" and result in residual stresses, Distortion—a closely related concept to residual stress, distortion is the elastic or plastic deformation of material under the action of thermal and residual stresses. It can result in irrecoverable displacement and bulk movement of material thereby changing the final shape of the component and creating deviations from the intended shape.

It should be still further recognized that for additive manufacturing processes there are process inputs that are controllable or are otherwise user-selectable. Many of these are identical to the process properties discussed above. Examples of such user controllable inputs include the following: Power, Travel speed, Focal and spatial energy distribution characteristics, BAM—beam active parameter—or how focal characteristics change with depth, Deflection and scan methods by lasers and electron beams. Laser deflection and scan methods include: Details and construction of the scan head, Galvanometer controls, F-theta lens or other focal lenses or strategies, Other mirrors or filters, and Dichroic mirrors or coatings, if any. Electron beam deflection and scan methods include: Deflection frequency, Magnetic deflection and focusing, Electrostatic deflection and focusing, Anode—cathode geometry, Electron gun type and design, Thermionic filament, type and geometry; Temporal energy distribution that include CW— continuous wave, Pulsed, Q-switched and otherwise modulated over time. Beam control can also include scan strategies that include choices of hatch spacing, hatch pattern and interlayer hatch pattern rotation angle. In some embodiments, multiple beams can be controlled. When multiple independently controlled lasers are being controlled, each with its own scan head, acting either completely independently or in coordination with other independent laser heads. In some cases, a very fast scan head with low inertia galvanometers can be used to create multiple "hot spots" with the same laser beam by "multiplexing" or fractionally and proportionally dividing the laser amongst the various hot spots. When multiple electron beams are being controlled, the ability to deflect charged particles at very high rates allows the creation of multiple hot spots from a single higher power electron beam and to modulate these precisely over any arbitrary temporal pattern as well as a controllable spatial pattern.

Powder distribution
   Layer thickness
   Recoating arm method and frequency of recoating
   Powder feeding and dispensing methodology and apparatus Preheating
    Preheating using platen heaters for baseplate
    Preheating using beam scan patterns under very defocused conditions and at low power
    Other forms of preheating
Build strategy
    Number of components in a build
    Orientation of individual components within a build
    Ability to deal with given lengths of unsupported overhangs
    Scaffold and support structure construction and design
    Optimization of support structure for a given part geometry, part configuration within a build For the physical phenomena associated with additive manufacturing, it is useful to consider various characteristic times which could be associated with the various physical phenomena. There are many examples of manufacturing processes involving the addition of heat on a relatively rapid timescale and the response of the material over a relatively slower timescale. For example, consider the autogenous welding of a part (i.e. no addition of material) comprising a scanning heat source moving rapidly over the joint between the two metal surfaces to be joined. Assume that the diameter of the heat source is D and the travel speed of the heat source is V. Therefore, the characteristic time of interaction between the heat source and the pieces of metal to be joined is described by the following equation:

$$t_{heat\ source} = \frac{D}{V} \quad (1)$$

It is seen that for very small D and very large V, this characteristic time of interaction of the heat source with the workpiece can be very small. For example, in laser powder bed additive manufacturing processes like direct metal laser sintering (DMLS) and SLS (selective laser sintering), the diameter of the heat source could be 0.1 mm or smaller, and the scanning speed of the heat source could be 1000 mm/s or faster, and therefore the characteristic interaction time of the heat source with the workpiece could be much less than 1 ms and could be close to 100 microseconds.

With respect to the material response, for the aforementioned laser powder bed processes, the material response will be dominated by heat conduction. The characteristic time for heat conduction is given by the following equation:

$$t_{material\ response} = \frac{X^2}{4\alpha} \quad (2)$$

Where X is a characteristic length over which heat conduction occurs, and $\alpha$ is the thermal diffusivity of the material. For many metals, the thermal diffusivity is on the order of $10^{-6}$ to $10^{-8}$ m$^2$/s. The appropriate characteristic distance to assume would be the powder layer thickness. But in general it is experimentally observed that the material below the powder layer is also re-melted, and therefore a larger characteristic distance is not unwarranted. If we take the characteristic distance to be the same as the beam diameter which is assumed to be 100 microns, and if we examine the range of thermal diffusivities, then the characteristic times for the material response is on the order of 2.5 milliseconds on the fast end to 0.25 seconds on the slow end. Therefore, it is seen that the characteristic time for the heat source—material interaction is 25 to 2500 times faster than the time required for the heat to diffuse away from the hot region into the surrounding material.

This is a universally observed phenomenon for rapid thermal processes such as laser welding, electron beam welding, and even many arc welding processes where the travel speed of the arc is high or the energy density of the arc is high. This is also a prevalent process condition for many additive manufacturing processes that arte based on lasers and electron beams and involve the addition of material either through a sequentially layered and melted or sintered powder bed or the direct addition of material through wire fed by a mechanical wire feeder or powder being fed by a nozzle where the powder may by fluidized, carried, or otherwise entrained in an inert gas stream.

There are also other characteristic times which will influence the consolidation of the powder bed and the possible occurrence of defects. The two most important such timescales relating to various fluid phenomenon are those governed by capillary effects and those governed by inertial effects. The capillary or viscous timescale associated with the breakup or consolidation of a Newtonian Fluid is given by:

$$t_{capillary} = \frac{\eta \cdot L}{\sigma} \quad (3)$$

Where $\eta$ the dynamic viscosity, L is a characteristic length for the process, and $\sigma$ is the surface tension of the liquid metal. For a characteristic length of 100 microns and assuming representative values of viscosity and surface tension for metals, we find that the capillary time is generally less than 1 microsecond.

Another important time scale is associated with the Rayleigh time, or the time scale associated with a low viscosity fluid being acted upon by inertial and surface tension forces. For example, this time scale governs the breakup or consolidation of droplets, or the time scale associated with the return of a fluid surface to equilibrium after a disturbance, assuming viscosity is a negligible effect as compared to inertial and surface tension forces. The equation for the Rayleigh time is given by:

$$t_{Rayleigh} = \sqrt{\frac{\rho \cdot L^3}{\sigma}} \quad (5)$$

Where $\rho$ is the fluid density, $\sigma$ is the surface tension, and L is a characteristic length scale. Again taking L to be 100 microns and assuming typical physical properties for molten metals, we get that the Rayleigh time is on the order of tens to hundreds of microseconds. This is a lot longer than the capillary time, but still shorter than the heat conduction time. So generally for the conditions which could be expected in additive manufacturing, it is found that:

$$t_{material\ response} > t_{Rayleigh} > t_{Capillary} \quad (5)$$

This means that generally the consolidation mechanisms of the molten material are faster than the heat conduction time, and therefore the process is dominated even on heating by heat conduction and not fluid effects. This also means that the width of the molten region at a given power level and beam diameter is also dominated by the heat conduction time.

Other thermal—related times of interest and significance are the adiabatic melting time and the adiabatic vaporization time. These are measures of how long it would take to melt and to vaporize a quantity of material in the absence of all thermal losses such as heat conduction. The adiabatic heating time is given by:

$$t_{adiabatic\ melt} = \frac{\frac{\pi \cdot D^2}{4} \cdot d \cdot \rho_{powder} \cdot [C_{P,solid} \cdot \Delta T_{melt} + L_{melt}]}{\epsilon \cdot P_{beam}} \quad (6)$$

Where D is the beam diameter, d is the material layer thickness of powder to be sintered, $\rho_{powder}$ is the powder bed density, $C_{P,solid}$ is the average specific heat capacity of the solid powder, $\Delta T_{melt}$ is the temperature difference between room temperature and the melting point of the material (in deg. K), $L_{melt}$ is the latent heat of melting, $\epsilon$ is the coupling efficiency of the beam to the material, and $P_{beam}$ is the beam power. In an entirely analogous manner, the adiabatic vaporization time is given by the following expression:

$$t_{adiabatic\ vapor} = \frac{\frac{\pi \cdot D^2}{4} \cdot d \cdot \rho_{powder} \cdot \begin{bmatrix} C_{P,solid} \cdot \Delta T_{melt} + L_{melt} + \\ C_{P,liquid} \cdot \Delta T_{vapor} + L_{vapor} \end{bmatrix}}{\epsilon \cdot P_{beam}} \quad (7)$$

Where D is the beam diameter, d is the material layer thickness of powder to be sintered, $\rho_{powder}$ is the powder bed density, $C_{P,solid}$ is the average specific heat capacity of the solid powder, $\Delta T_{melt}$ is the temperature difference between room temperature and the melting point of the material (in deg. K), $L_{melt}$ is the latent heat of melting, $C_{P,liquid}$ is the average specific heat capacity of the liquid, $\Delta T_{vapor}$ is the temperature difference between the melting point of the material and the vaporization point of the material (in deg. K), $L_{vapor}$ is the latent heat of vaporization, $\epsilon$ is the coupling efficiency of the beam to the material, and $P_{beam}$ is the beam power. Assuming thermophysical properties of nickel as an example, these various times are 3 microseconds for the adiabatic melting time, and 30 microseconds for the adiabatic vaporization time respectively.

Yet another time which is associated with cooling in the immediate vicinity of the molten region. This characteristic time is the local solidification time. It is given by:

$$t_{solidification} = \frac{\Delta T_{melt}}{\left(\frac{\partial T}{\partial t}\right)_{max}} \approx \frac{\Delta T_{melt}}{V \cdot \left(\frac{\partial T}{\partial x}\right)_{max}} \quad (8)$$

Where $\Delta T_{melt}$ is the temperature difference between room temperature and the melting point of the material (in deg K), $\left(\frac{\partial T}{\partial t}\right)_{max}$ is the maximum cooling rate which could be measured for an individual scan by a stationary sensor, for example, V is the beam travel velocity, and $$\left(\frac{\partial T}{\partial x}\right)_{max}$$

is the maximum thermal gradient at the liquid solid boundary, which could be measured through sensors looking down or in parallel with the optical train in a laser-based system, for example. For many of the cases of interest for metal AM, this local solidification time could be less than 1 millisecond but greater than 100 microseconds.

Yet still another time which could have relevance to the evolution of distortion and residual stress within the process is the thermal relaxation time for the part, which is given by:

$$t_{relaxation} = \frac{L^2}{4\alpha} \quad (9)$$

Where L is a characteristic length for the part being printed and $\alpha$ is the thermal diffusivity of the material. For example if the characteristic length is a millimeter to a centimeter then this characteristic relaxation time could be on the order of 2.5 to 250 seconds. This is the timeframe over which thermal relaxation occurs over macroscopic lengths.

For manufacturing processes such as those discussed above that add heat and that achieve significant temperatures such that there are radiative emissions coming from the process, another mode of sensing is spectroscopy. The radiation that is thus emitted is both blackbody radiation as well as characteristic radiation. The blackbody radiation is a function of the temperature of the process and is governed by Planck's Equation:

$$I(v, T) = \frac{2hv^3}{c^2} \frac{1}{e^{\frac{hv}{kT}} - 1} \quad (10)$$

Where I is the intensity of radiation emitted per unit time per unit area normal to the emitting surface, T is the absolute temperature of the surface in degrees Kelvin, h is the Planck constant, k is the Boltzmann Constant, c is the Speed of Light, and v is the frequency of the radiation emitted. The relationship between the absolute temperature and the wavelength of the maximum emitted radiation is given by Wien's Displacement Law:
Where b is a constant.

$$\lambda_{max} = \frac{b}{T} \quad (11)$$

Furthermore there are several physical phenomena that can be considered as the radiated energy leaves the hot region, propagates through space, arrives at the sensor, is collected by the sensor, and is converted into an electrical signal. These physical phenomena include, but are not limited to: spectral response of the sensor, frequency of the sensor, field of view of the sensor, distance between the sensor and heat source/material interaction, characteristics of optical components in optical path of the sensor.

In addition to the blackbody radiation which is a function of temperature, there are characteristic radiation peaks in the spectral data which are due to photons emitted as a result of specific electronic transitions between quantum states of atoms excited by multi-photon processes or by direct electron collisions. These are called characteristic because they are characteristic to a particular atom and ionization state(s). These will manifest in the spectral data as specific peaks at specific wavelengths. There will often be multiple peaks associated with various elements and electronic transitions, and as a result this spectral data can quickly get very complex.

If the integration times of the spectrometer as well as the incident beam time of the laser were absolutely identical and the spectrometer always saw optical emissions for a given fixed time when the laser was within the field of view of the spectrometer, and if the same chemical species were present in the vaporized plume in the same atomic percentages, then the absolute value of the intensity of the optical emission at a given characteristic spectral line could be used as an indicator of energy coupling to the powder bed. However the following intervening factors prevent the use of the absolute value of spectral peaks as a feature that could be used to gage the extent of energy coupling between the incident energy beam and the powder bed during an additive manufacturing process:

1) The spectrometer will have a certain finite field of view over a certain region of the powder bed. Depending on the scan pattern of the laser or electron beam, the beam will intersect this fixed field of view for different periods of time. Thus, during a fixed shutter open time (also equal to the spectrometer integration time), the laser or electron beam will not intersect the spectrometer field of view in the same way or the same number of times. This will result in variations in the intensity signal 2) The atomic concentration of species that are either excited neutral species or ionized and are giving off characteristic radiation will vary as a function of the power level. Also, in a multi-element, multi-component alloy, there could be several elements contributing to the spectral lines and several of these elements may have closely spaced lines, especially for transition metals found in most common engineering alloys that have complex electronic transition states and hence complex associated spectra. This complex variation of atomic species that are responsible for the characteristic emissions—both in terms of atomic composition and relative atomic percent—results in variations in the absolute value of the spectral intensity at any given wavelength which makes it difficult to utilize this absolute value as a feature.

As a result of these and possibly other intervening factors, it is desirable to select another feature that could allow the characteristic spectral data to be used as a discriminator to see when the energy coupling between the laser or electron beam and the powder bed may be optimal. The FFT—Fast Fourier Transform—of the spectral data will indicate where any given spectrum is undergoing more rapid change in value. When there is a greater atomic concentration of a given excited neutral or ionized species in the plume above the energy beam/powder bed interaction zone and these species are emitting characteristic radiation, it is expected that the corresponding spectral peaks will be sharper and will therefore have higher values of FFT intensity at a given inverse wavelength. Conversely, when the characteristic emissions are lower due to the fact that there are relatively fewer excited species due to a more optimal energy coupling, then the relative peak at a given wavelength will be broader and the background blackbody radiation will play a more dominant role in the spectral intensity at that given wavelength. Therefore the FFT intensity peak under such conditions at the same inverse wavelength would be lower than that observed otherwise. Therefore the FFT intensity at some intermediate inverse wavelength (which will depend on the alloy composition) could serve as an indicator of the relative coupling efficiency of the incident energy beam to the workpiece.

Additive manufacturing processes may be symbolically represented as a logical operator which acts on four distinct sets:

$$\{\text{outcomes of } AM \text{ process}\} \equiv \qquad (12)$$
$$\varphi \begin{bmatrix} \{\text{intrinsic material properties}\}, \{\text{extrinsic powder properties}\}, \\ \{\text{process properties}\}, \{\text{in-process physical behaviors}\} \end{bmatrix}$$

FIG. 1 shows a flow chart that further elaborates the meaning of Equation 12. The process inputs 100 are the "knob settings" or controllable process inputs that are programmable or otherwise user-selectable The intrinsic material properties 101 of the alloy may also be viewed as process inputs which are independent of any other properties of the powders or the process. The process properties 102 are determined by the process inputs 100 to the largest extent, but have a slight influence from the intrinsic material properties 101. The process properties 102 and the extrinsic powder properties 103 influence each other. For example, the method of application of the next layer of powder, also known as recoating, is a process property 103. But it influences extrinsic powder properties 103 such as powder bed density and layer thickness. Conversely, extrinsic powder properties 103 such as particle size distribution, particle size and shape, etc influence how the recoating process works, which is a process property 102. There will in general also exist environmental disturbances 104 which could be viewed as either uncontrolled process inputs which were not detected or regulated by any other engineering or administrative controls, or they could represent unmodeled dynamics in the additive manufacturing process itself. In the former case of uncontrolled process inputs which were not quantified or controlled, these could be categorized as "known unknowns" because their category or type is known, but the level or magnitude of the inputs was unknown or otherwise did not meet a specification. In the latter case of unmodeled dynamics, these represent "unknown unknowns" because we do not have any a priori knowledge of their type or category. We can only see their effects a posteriori as they influence the set of additive manufacturing process outcomes 106. The process properties 102, the extrinsic powder properties 103, and the environmental disturbances 104 all influence the additive manufacturing process 105. The additive manufacturing process 105 then produces a set of process outcomes 106 which could range from nominal, off-nominal, or could involve a wide array of specifically classified and categorized off-nominal conditions.

Figure 2:
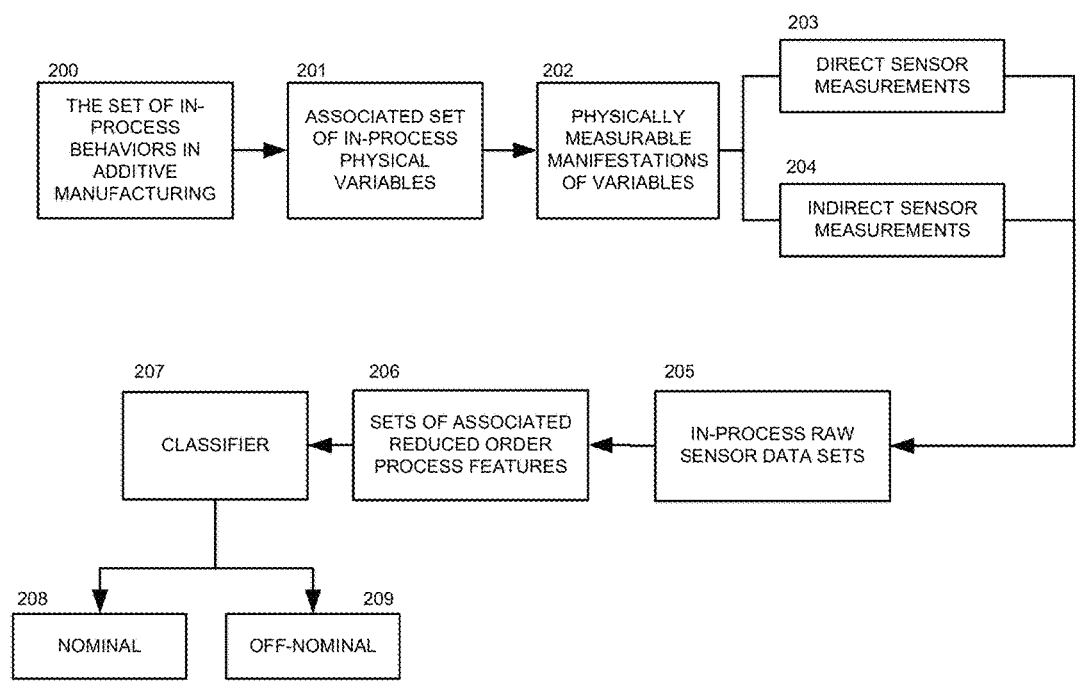

When it comes to process sensing of any kind, whether it is optical or non-optical, the sensor data tells us something about the in-process physical behaviors and their current state, state of evolution, or the cumulative results of past states. However these physical behaviors cannot be measured directly; they can be characterized by their associated set of in-process variables. This reality is further illustrated in FIG. 2. The set of in-process physical behaviors 200 comprises all physical behaviors which occur during the additive manufacturing process which could influence its outcome and the quality of the resultant deposit. There will be an associated set of in-process variables 201 which directly track the evolution or characterize the current state of these in-process physical behaviors 200. However not all of the in-process physical behaviors 201 may be directly observable. For example, consider the in-process behavior 200 of wetting of unmelted powders by incipient liquid metal which is formed in the very early stages of irradiation by the moving heat source. The in-process variable 201 which most directly characterizes this process is the dynamic contact angle between the liquid metal and the solid powder. However this variable is not directly observable. Therefore it is found that in general there will also exist a set of physically measurable manifestations 202 of the in-process variables 201 which correspond to quantities which could be measured by one or more sensor modalities. So in the example discussed above, when enough powders are wetted and a resulting weld pool is formed, there will be optical emissions from this weld pool, which is a physical manifestation 202 that tracks the evolution of how big the weld pool is at any given time, but now does not directly or unambiguously point back to the specific in-process variable 201 of wetting angle between liquid and solid.

Associated with each physically measurable manifestation 202 of the in-process variables 201, there could be both direct sensor measurements 203 as well as indirect sensor measurements 204 which characterize the specific physical manifestation 202 for each in-process variables 201. It is therefore seen that there are two levels of uncertainty and potential lack of either measurement resolution or accuracy. The in-process variables 201 cannot be directly measured but only the physical manifestations 202 of these variables can be measured. At the next level of uncertainty, there may not always exist direct sensor measurements 203 of these physical manifestations 202, and a series of indirect sensor measurements 204 may have to be used instead. In either event, the set of direct sensor measurements 203 and indirect sensor measurements 204 in turn comprise the aggregated set of in-process raw sensor data 205.

From this raw sensor data 205, it is possible to extract a multitude of reduced order process features 206 using a multiplicity of feature extraction techniques. For the purposes of this discussion "reduced order" refers to one or more of the following aspects: data compression, i.e. less data in the features as compared to the raw data; data reduction, i.e. a systematic analysis of the raw data which yields process metrics or other figures of merit; data aggregation, i.e. the clustering of data into discrete groupings and a smaller set of variables that characterize the clustering as opposed to the raw data itself; data transformation, i.e. the mathematical manipulation of data to linearly or non-linearly map the raw data into another variable space of lower dimensionality using a transformation law or algorithm; or any other related such techniques which will have the net effect of reducing data density, reducing data dimensionality, reducing data size, transforming data into another reduced space, or all of these either effected simultaneously.

Once these feature extraction methods 206 have been applied to the raw sensor data 205, the results could be sent to a classifier 207 which is capable of grouping the results as being either nominal 208 or off-nominal 209. The classifier 207 could use a plurality of classification methods including, but not limited to: statistical classification, both single and multivariable; heuristic based classifiers; expert system based classifiers; lookup table based classifiers; classifiers based simply on upper or lower control limits; classifiers which work in conjunction with one or more statistical distributions which could establish nominal vs off-nominal thresholds based on confidence intervals and/or a consideration f the degrees of freedom; or any other classification scheme 207 whether implicit or explicit which is capable of discerning whether a set of feature data 206 is nominal 208 or off-nominal 209. For the purposes of this discussion, "nominal" will mean a set of process outcomes which were within a pre-defined specification, which result in post-process measured attributes of the parts thus manufactured falling within a regime of values which are deemed acceptable, or any other quantitative, semi-quantitative, objective, or subjective methodology for establishing an "acceptable" component.

Figure 3:
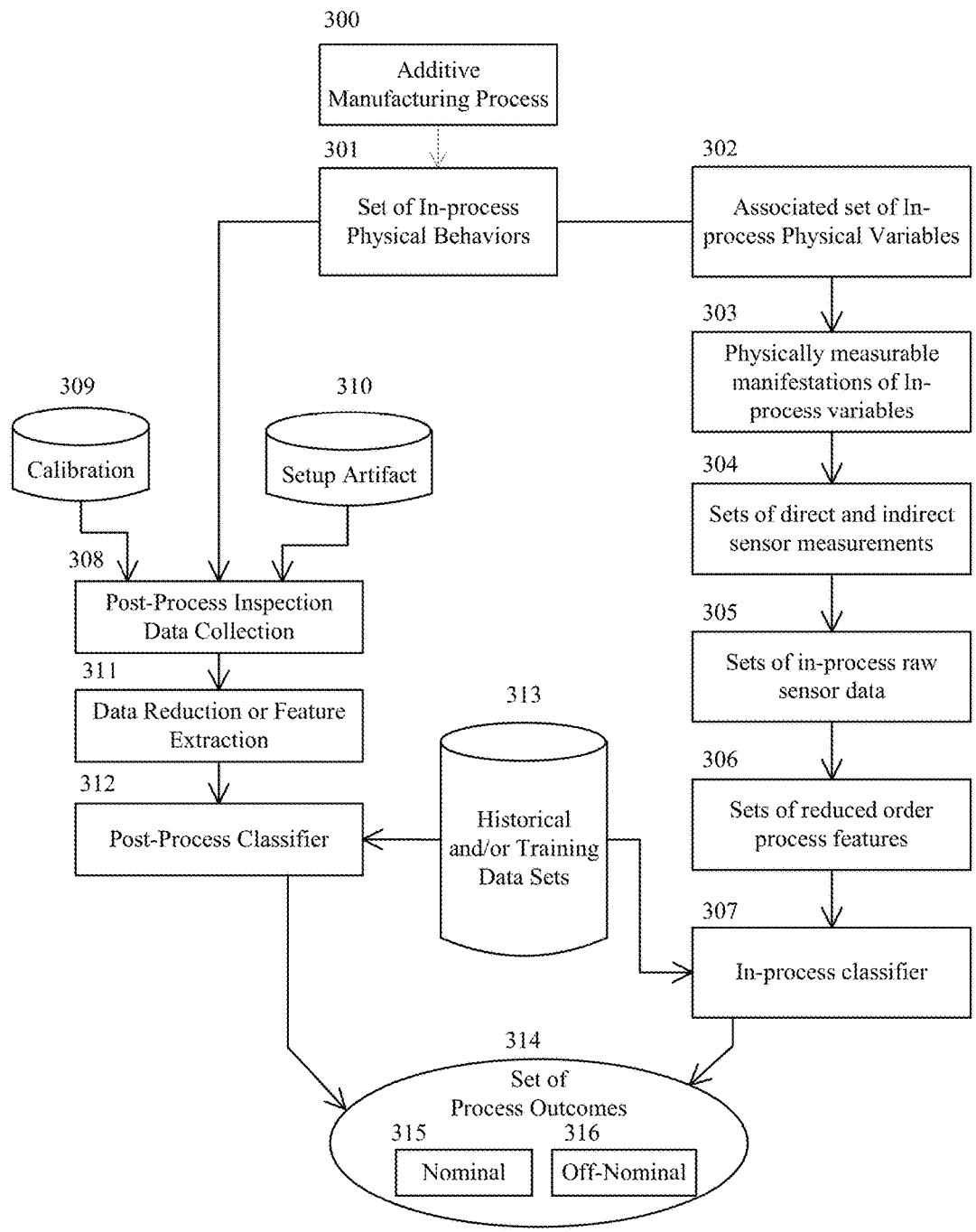

It is seen that the critical utility of any in-process data, features, and associated classification lies in the ability to discern nominal vs. off-nominal conditions. It is useful however to more closely examine precisely what it means to declare a set of process outcomes as "nominal" based on the results of in-process data and associated analysis by examining the flowchart as described in FIG. 3. The additive manufacturing process 300 has associated with it a set of in-process physical behaviors 301. As the nature of these behaviors has been previously discussed this discussion will not be repeated herein. Also as discussed before, the in-process physical behaviors 301 have a set of associated in-process physical variables 303 that in turn have associated with them physically measurable manifestations 304. The manifestations 304 are measured by a set of direct or indirect sensor measurement 304 to generate an aggregated set or sets of raw sensor data 305. In turn through the application of a wide array of possible feature extraction methods a set of reduced order features 306 is derived from the raw data sets 305. These features are then in turn provided for additional analysis to the in-process classifier, i.e. the classifier which acts on the set of features 306 which have been derived through the chain of events described above and may be said therefore to track the evolution or characterize the current or past states of the in-process physical behaviors 301.

Alternatively, another series of steps could be undertaken to assess the results of the in-process physical behaviors 301. For example, post-process inspection data 308 could be collected using a wide variety of non-destructive or destructive post-process inspection techniques. As a critical and closely associated step with collecting such post-process inspection data 308, there could be calibration steps and data 309 or setup artifacts and associated data 310. These are two enabling sets of data or physical objects which help to improve the accuracy or resolution of the post-process data set 308. Then in an exactly analogous manner to the in-process case, data reduction or feature extraction 311 can take place so that the raw post-process data 308 can be turned into sets of reduced order post-process features 311. These features are provided to a post-process classifier 312 in exactly the same manner that the in-process features 306 were provided to the in-process classifier 307.

For both post-process and in-process classifiers (312 and 307 respectively) it is generally not possible a priori to separate the set of process outcomes 314 into nominal 315 or off-nominal 316 subsets. In general, there can exist some a posteriori data, expert knowledge, or some other historical and/or training data set or set 313 which would enable the classifiers 312 and 307 to act upon their respective feature sets 311 and 306 so as to separate the set of process outcomes 314 into nominal 315 and off-nominal 316 subsets.

Figure 4:
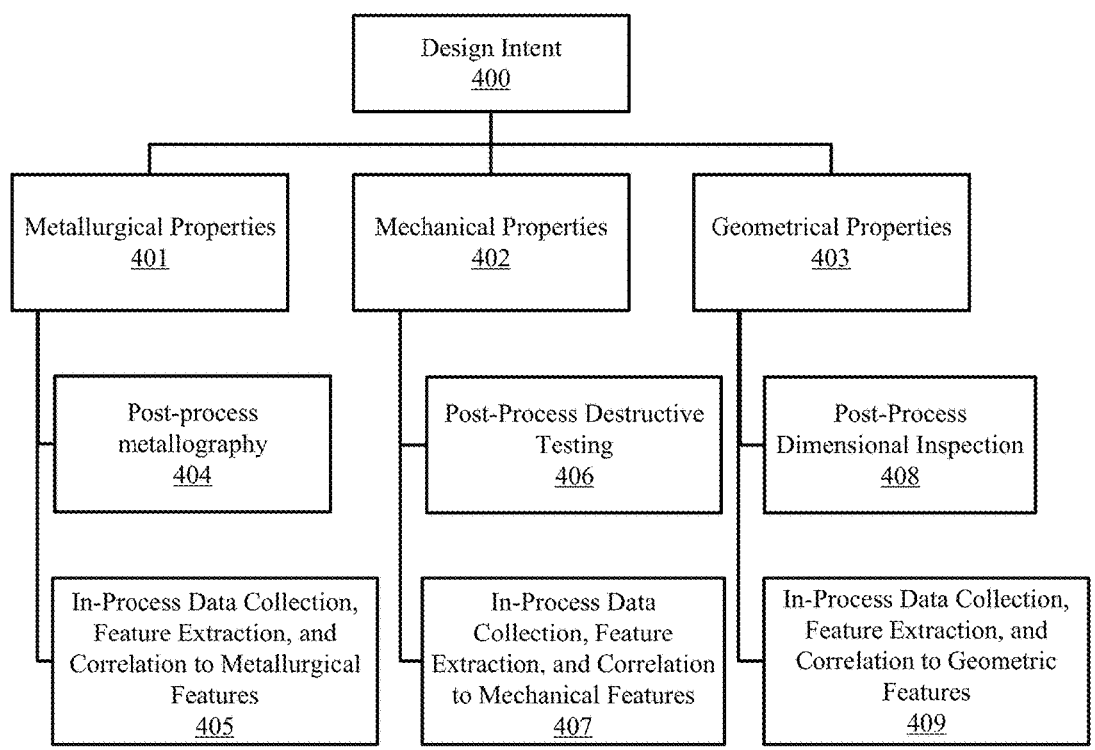

In the context of this present invention, one of the main objectives and aims is to establish how in-process metrics could be used to classify process outcomes as nominal or off-nominal. Currently in manufacturing processes including additive manufacturing, only post process part acceptance methods are used. The overall methodology of post-process inspection is explained in greater detail in FIG. 4 The Design Intent 400 is quantified by one of three general categories. First, the metallurgical properties 401 specify such quantities as grain size, composition precipitate structure, defect structure, and other microstructural features and attributes which characterize the structure of the material which comprises the manufactured article. The second category of properties is the set of mechanical properties 402. These could include, but are not limited to, such quantities as elastic properties and moduli, static yield strength, elongation and ductility, low cycle fatigue life, high cycle fatigue life, thermo-mechanical fatigue life, crack growth rates under various loading conditions, creep and rupture properties, and other mechanical performance criteria under specialized loading conditions. The third category of properties is the set of geometric properties 403. These could include shape, size, and texture among other geometric properties.

Now coming to the various methods of measuring, validating and verifying the three categories of properties described above, there are destructive and non-destructive methods, as well as in-process and post-process methods. For example in the evaluation of metallurgical properties 401, the most common methods involve the use of destructive evaluation techniques based on Metallography 404, or the microscope analysis of material structure. Alternatively, it is possible to use an in-process approach 405. In this in-process approach 405, data from the Additive Manufacturing Process is collected in-situ either continuously, intermittently, or at specific discrete intermediate states during the manufacture of the Article. Then features are extracted from this in-process data. The extracted features are then further correlated to microstructural features, and the ability of the in-process features to predict the corresponding microstructural features is validated and verified. Once this validation and verification is completed, then the in-process approach 405 can become predictive of metallurgical properties 401. The methods for testing and evaluating Mechanical Properties 402 usually involve destructive methods of Post Process Destructive Mechanical Testing 406. Such methods involve a wide variety of testing methods and equipment at a wide range of strain rates, loading rates, and thermal conditions.

Finally coming to the methods and techniques for evaluating the Geometric Properties 403, the most common is the use of Post Process Dimensional Inspection 407. This could be accomplished using a variety of measurement instruments which could be simple gages, contact geometrical measurement machines such as CMMs—coordinate measurement machines, or non-destructive geometric measurement methods such as CAT scanning—Computer Aided Tomography, or various optical scanning techniques which are also non-contact. Alternatively there is a body of techniques which is the subject of this present invention, namely in-process characterization of geometric properties 408. In such in-process characterization 408, first data is collected from a variety of sensors. Then features are extracted from this data which can be correlated to the Geometric Properties 403 of the Article. The data collected and the associated features extracted may be collected continuously, intermittently, or at specific discrete intermediate states occurring during the manufacture of the Article. Lastly, there is a verification and validation step in which in-process data 408 are compared to post process inspection data 407 to verify that the in-process data 408 is capable of verifying the Geometric Properties 403 correspond to Design Intent 400.

Therefore in order to be used in a quality inference or process control scheme, in-process metrics and features derived from in-process data can correlate in some fashion to metrics and features derived from post-process inspection and evaluation methods. So to integrate and expand upon all of the concepts shown in previous figures and discussed above, some embodiments of the present invention utilize a correlative classifier that combines in-process classifiers and post-process classifiers into a unified classifier that enables in-process data to be predictive of post-process measured properties or attributes of a component. This is schematically shown in FIG. 5 which integrates materials from the previous discussions and figures.

Figure 5:
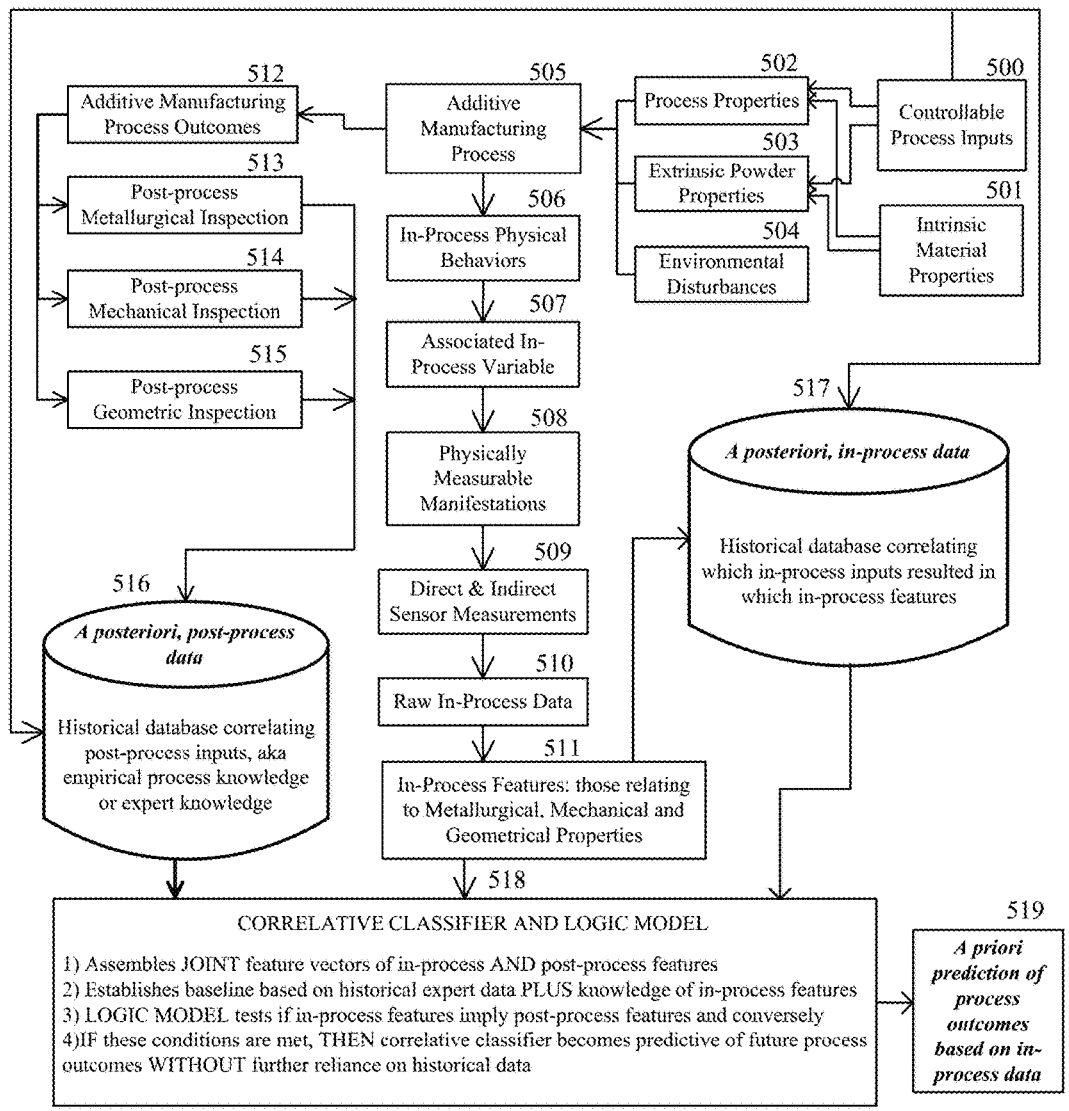

In FIG. 5 the additive manufacturing process has inputs 500 that comprise user selectable values for various machine settings or other user selectable features within the machine or process. Examples would be the programmed beam power, travel speed, etc. In addition the material that is to be used in the additive mfg. process has certain intrinsic material properties 501. These properties include melting point, specific heat, thermal conductivity, etc. In addition to these, there are process properties 502 which are properties that are dependent on the inputs 500 and the intrinsic material properties 501. Examples of such properties could include the actual spatial distribution of heat from the moving heat source in Watts per square cm as a function of position. Additionally the powder bed has extrinsic properties 503 that are not a function of the alloy but rather the powder form as well as how the powder is distributed in the additive manufacturing process. Examples of such properties include particle size distribution and powder density in the powder bed. There will invariably be environmental disturbances 504 that are either uncertainties in known quantities such as laser power or may be unknown dynamics such as variations in the laser absorptivity by the powders for unknown reasons.

All of these factors 500-504 are collectively the inputs for the additive manufacturing process 505 which could also include post-processes such as heat treatment or hot isostatic pressing (HIP). Therefore the definition of manufacturing process herein is not just limited to the additive manufacturing process itself but could include additional post-process steps. The manufacturing process 505 is characterized by in-process behaviors 506. These in-process behaviors 506 have associated with them in-process variables 507. As previously discussed these variables 507 may not be directly observable but their physically observable manifestations 508 will be detectable by direct or indirect sensor measurements 509. These measurements 509 will generate a large volume of raw in-process data 510. Then through a variety of algorithmic methods, a set or multiple sets of in-process features 511 are derived.

The manufacturing process 505 itself will produce process outcomes 512 which could be for example acceptable part, unacceptable part, excessive porosity, etc. These process outcomes 512 can be characterized by the in-process features 511 but can also be characterized by post-process inspection and evaluation techniques 513-515. These techniques include metallurgical inspections 513, mechanical inspections 514 which examine mechanical properties, and geometric inspections 525 which aim to measure part geometry. The results of all of these post-process measurements can be stored in a post-process database 516 that correlates the post-process results to the controllable process inputs 500. This is typically what constitutes expert process knowledge in the way additive manufacturing or any other manufacturing process is conducted at present. Similarly, a database of in-process features 517 could be established which correlates the in-process features 511 to the controllable process inputs 500 which resulted in the process outcomes 512 which generated the in-process features 511.

Some embodiments of the present invention then establish a correlative classifier and a logical model 518 which utilizes the data from both the post-process 516 and the in-process 517 databases. This classifier and logic model 518 has four principal functions:

- It assembles JOINT feature vectors of in-process AND post-process features
- It establishes a baseline based on historical expert data PLUS knowledge of in-process features associated with given process inputs KNOWN to produce certain process outcomes
- The LOGIC MODEL tests if in-process features imply post-process features and conversely
- IF these conditions are met, THEN CORRELATIVE CLASSIFIER becomes predictive of future process outcomes WITHOUT further reliance on historical data As a result of step 4 described above, the correlative classifier 518 can become predictive of process outcomes 512 based on in-process feature data 511. This state is shown in 519. The method by which in-process data and associated in-process features could become predictive of process outcomes as well as part quality has been described in detail above. Now it is instructive to examine the types and categories of sensor data which could be possible within the context of additive manufacturing. At the highest level of consideration, the following sensors are possible and the physical behaviors they could measure are listed in the table below.

| SENSOR CATEGORY | SENSORS | PHYSICAL BEHAVIORS IT COULD MEASURE |
|---|---|---|
| Force and vibration | Accelerometers vibration sensors mechanical shock sensors strain gauges piezoelectric sensors | The uniformity of the powder addition process which typically involves a mechanical arm that spreads the powders. Any irregularities in the arm, the mechanical motion, the spreading action, or the arm hitting previously deposited layers could be important to indicate possible non-uniformities in the powder bed as a result of errors in this mechanical spreading action. |
| Contact thermal | thermocouples thermistors resistance thermal detectors (RTDs) | The powder bed temperature as well as other temperatures in the equipment, the processing chamber, or other aspects of the manufacturing process could be sensed and detected with these sensors. This kind of data is valuable to know the macro thermal state of the process, including preheating, as well as for machine diagnostics and preventative maintenance for the machine itself |
| Non-contact thermal | single color pyrometer two or multi-color pyrometer | These sensors measure both process as well as ambient powder bed temperatures and could do so in the frame of reference of the laser or in a stationary reference frame. They can measure |
| Non-contact thermal | thermal imaging camera ratio pyrometers fiber optic pyrometers | very fast thermal transients associated with heating, melting and cooling as well as slower thermal transients at longer timescales as was discussed previously. |
| Optical | photodiode spectrometer | These sensors could again be in a moving or a fixed reference frame. Photodiodes measure intensity of light emissions over a given range of wavelengths and could be correlated to such features as weld pool size and/or temperature. They could also detect anomalies such as regions where the laser power absorption suddenly changes, or areas where the power absorbed otherwise fluctuates. Spectrometers can also perform chemical analysis of the vaporized and either ionized or unionized plasmas or vapors associated with the additive manufacturing process |
| Optical | high speed camera camera linear camera other optical imaging systems | These types of sensors could be used again in the frame of reference of the beam or in a stationary frame. They could measure such things as weld pool size and shape, the shape and precise metrology of the layer just deposited, irregularities in the manufacturing process, the integrity of the powder bed as new powder layers are applied, as well as other nominal and off-nominal process conditions |
| Other | laser ultrasonic eddy current ultrasonic acoustic emission | This category of sensors involves other or multiple physical phenomena. For example the laser ultrasonic could involve a laser interferometer which could directly interrogate the manufacturing process, or in conjunction with an |

| SENSOR CATEGORY | SENSORS | PHYSICAL BEHAVIORS IT COULD MEASURE |
|---|---|---|
| | | excitation source could be used to directly measure mechanical properties of the deposit as the process build is occurring. Eddy current sensors can similarly measure the integrity of the build if they are swept over the built up part. Similarly it may be possible to perform in-situ ultrasonic measurements. Acoustic emission measurements may be sensitive to high speed metallurgical phenomena such as dislocation motion and cracking and would be attached to the base of the part being built up |

Figure 6:
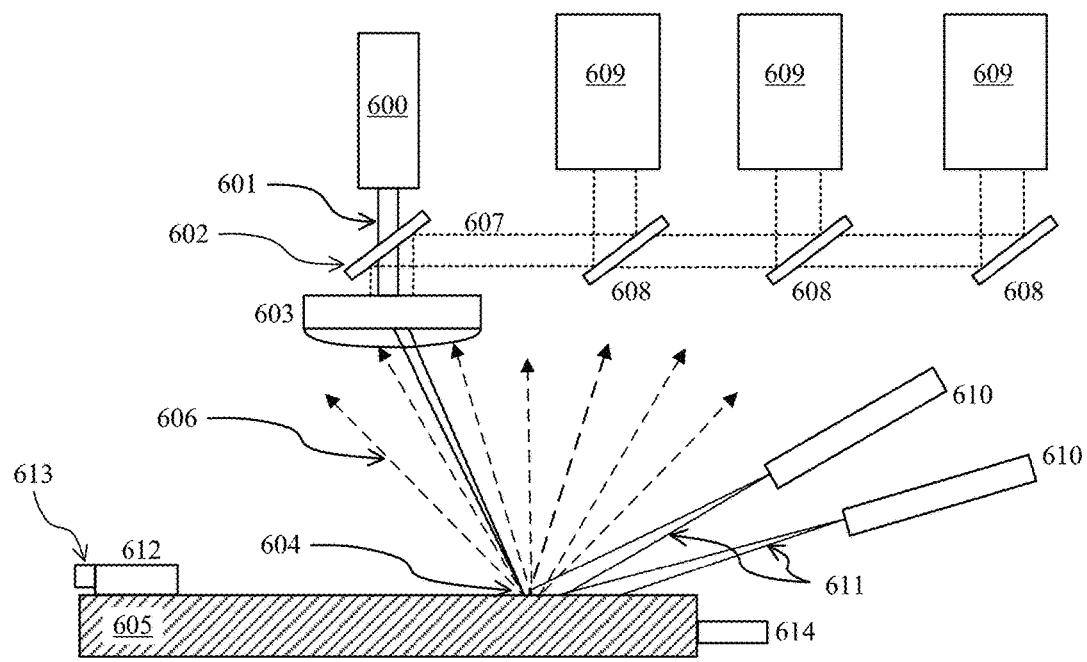
FIGS. 6-9 illustrate a number of views of exemplary machinery and sensors associated with additive manufacturing processes.

These sensors and some of their possible configurations are shown in FIG. 6. Consider for the time being the instance of an additive manufacturing process that utilizes lasers as the heat source. The laser 600 emits the laser beam 601 which passes through a partially reflective mirror 602 and enters a scanning and focusing system 603 which then projects the beam to a small region 604 on the work platform or the part being built up 605. Optical energy 606 is emitted from the beam interaction region 604 on account of high material temperatures. Some of this energy goes back through the scanning an focusing system 603 and is reflected by the partially reflective mirror 602 resulting in an optical signal 607 which may be interrogated by multiple optical sensors 609 each receiving a portion of the optical signals 607 through a series of additional partially reflective mirrors 608. It should be noted that the collected optical signal 607 will not generally have the same spectral content as the emitted radiation 606 because the signal 607 has gone through multiple optical elements such as 603, 602, and 608 which each have their own transmission and absorption characteristics and thus would limit or other eliminate certain portions of the spectrum of energy radiated by the process 606. Examples of the optical sensors 609 include but are not limited to photo to electrical signal transducers such as pyrometers and photodiodes. The optical sensors 609 can also include spectrometers, and low or high speed cameras that operate in the visible, ultraviolet, or the infrared frequency spectrum. The sensors 609 are in a frame of reference which moves with the beam, i.e. they see all regions that are touched by the laser beam and are able to collect optical signals 607 from all regions of the build 605 touched by the laser beam 601. There can also be sensors 610 that are in a stationary frame of reference with respect to the laser beam 601. These stationary sensors 610 will have a given field of view 611 which could be very narrow or it could encompass the entire build area 605. Examples of these sensors could include but are not limited to pyrometers, photodiodes, spectrometers, high or low speed cameras operating in visible, ultraviolet, or IR spectral ranges, etc. The sensors 610 could also be sensors which combine a series of physical measurement modalities such as a laser ultrasonic sensor which could actively excite or "ping" the deposit with one laser beam and then use a laser interferometer to measure the resultant ultrasonic waves or "ringing" of the structure in order to measure or predict mechanical properties or mechanical integrity of the deposit as it is being built. The laser ultrasonic sensor/interferometer system can be used to measure the elastic properties of the material, which can provide insight into, for example, the porosity of the material and other materials properties. Additionally, the surface movement or other fluctuations of the weld pool can be measured based on the displacement of the weld pool surface. Additionally, the weld pool depth can be determined using the interferometry processes described herein. Components of the laser ultrasonic sensor/interferometer system can follow the weld pool or can be provided on their own scanning axis as appropriate to the particular implementation. As an example, in-line coherent imaging can be performed using embodiments of the present invention. Modulation of the laser beam used to melt the material can be used to provide one of the optical signals used in the interferometry process. Additionally, defect formation that results in material vibration can be measured suing the laser ultrasonic sensor/interferometer system.

Additionally, there could be contact sensors 613 on the mechanical device 612 which spreads the powders. These sensors could be accelerometers, vibration sensors, etc. Lastly there could be other types of sensors 614. These could include contact sensors such as thermocouples to measure macro thermal fields or could include acoustic emission sensors which could detect cracking and other metallurgical phenomena occurring in the deposit as it is being built. These contact sensors can be utilized during the powder addition process characterize the operation of the mechanical device 612, which can also be referred to as a recoater arm. Accordingly, non-uniformities in the surface of the spread powder can be detected and addressed by the system. Rough surfaces resulting from the powder spreading process can be characterized in order to repeat the powder spreading process in order to reduce or eliminate non-uniformities in the surface of the spread powder. In one implementation, a peak in the spread powder can be fused by the heat source, resulting in the subsequent layer of powder having a corresponding peak. At some point, the peak could contact the recoater arm, potentially damaging the recoater arm and resulting in additional spread powder non-uniformity. Accordingly, embodiments of the present invention can detect the non-uniformities in the spread powder before they result in non-uniformities in the manufactured part. One of ordinary skill in the art would recognize many variations, modifications, and alternatives.

Acoustic emission sensors operating, for example, in the range of 100 kHz to 400 kHz, can detect material properties that produce these high frequency acoustic emissions, for example, cracking of the sample. In-process acoustic emission thus provides insight into material properties that are not available using conventional techniques. As another example, heating and cooling rates can be measured using acoustic emission sensors based on material changes that produce high frequency acoustic emissions. Accordingly, embodiments of the present invention can measure defects being created in the material in real time using in-process measurements. In some embodiments, the acoustic emission sensors can be coupled to the build plate whereas in other embodiments, the sensors can be moved to contact solidified elements of the manufactured part to measure portions of the manufactured part as the powder bed moves away from the build plate. This method would also be applicable to thermocouples, thermistors, RTDs, and other sensors represented by 614.

Figure 7:
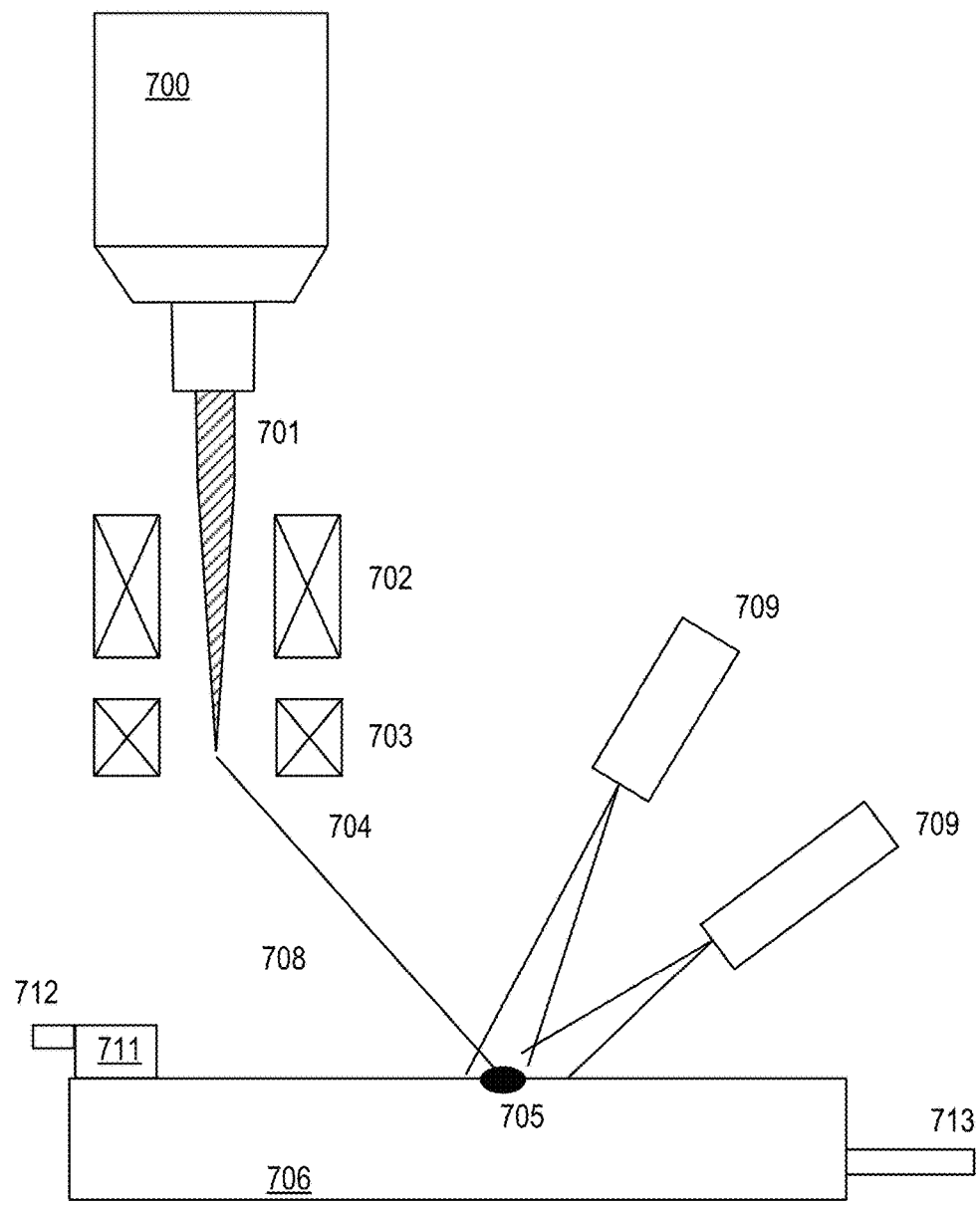

In the case of an electron beam system, FIG. 7 shows possible configurations and arrangements of sensors. The electron gun 700 generates an electron beam 701 that is focused by the electromagnetic focusing system 702 and is then deflected by the electromagnetic deflection system 703 resulting in a finely focused and deflected electron beam 704 which creates a hot beam-material interaction zone 705 on the workpiece 706. Optical energy is emitted 708 which could be collected by a series of sensors 709 each with their own respective field of view 710 which again could be locally isolated to the interaction region 705 or could encompass the entire build area 706. Additionally, the sensors 709 could have their own optical tracking and scanning system which could follow the electron beam 704 as it moves across the build area 706. Whether or not these sensors 709 have optical tracking or not, the sensors 709 could consist of pyrometers, photodiodes, spectrometers, and high or low speed cameras operating in the visible, UV, or IR spectral regions. The sensors 709 could also be sensors which combine a series of physical measurement modalities such as a laser ultrasonic sensor which could actively excite or "ping" the deposit with one laser beam and then use a laser interferometer to measure the resultant ultrasonic waves or "ringing" of the structure in order to measure or predict mechanical properties or mechanical integrity of the deposit as it is being built. Additionally, there could be contact sensors 712 on the mechanical device which spreads the powders 711. These sensors could be accelerometers, vibration sensors, etc. Lastly there could be other types of sensors 713. These could include contact sensors such as thermocouples to measure macro thermal fields or could include acoustic emission sensors which could detect cracking and other metallurgical phenomena occurring in the deposit as it is being built.

Figure 8:
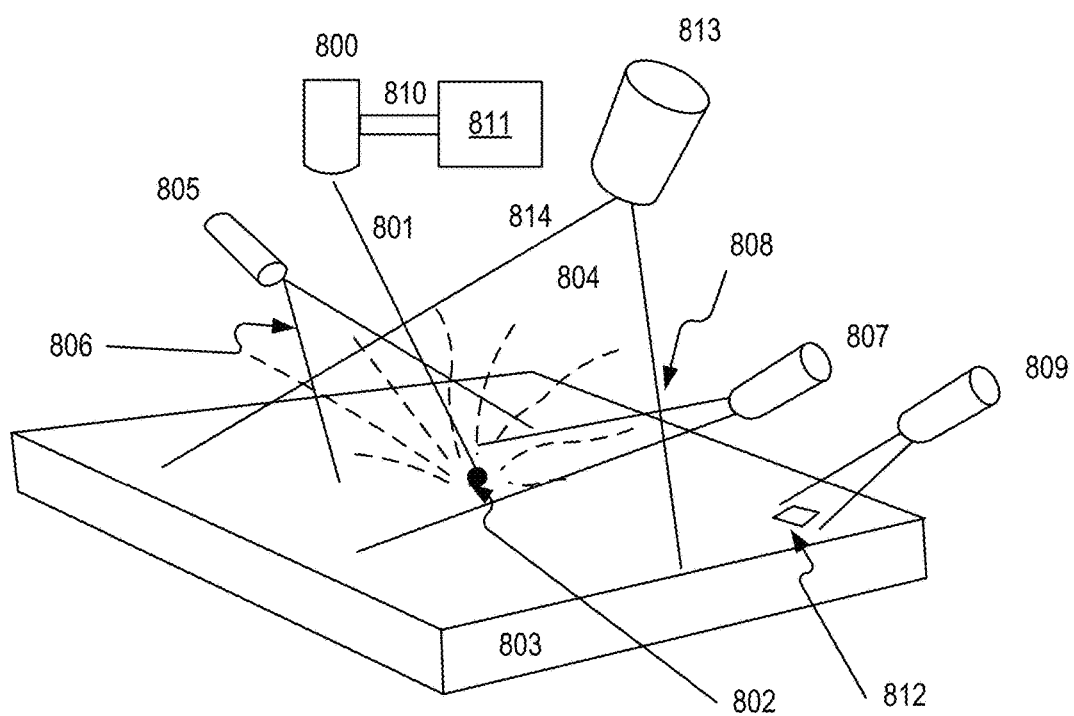

One specific sensor configuration which could be useful in practice is shown in FIG. 8. The electron beam or laser beam 800 generates a finely focused and deflected beam 801. This beam 801 creates a hot interaction zone 802 on the workpiece and build area 803 which again generates optical emissions 804. Two stationary sensors which could be any optical sensor but could specifically be photodiodes that are positioned 180 degrees apart. The first sensor 805 has a field of view 806 and the sensor 807 has a field of view 808. These fields of view could be narrow or broad, or in one specific instance they could cover the entire build area 803 thereby providing complete coverage and the ability to always see the hot interaction region 802 created by the focused deflected beam 801. In the case where the energy beam 800 is a laser beam, there is the additional potential of collecting an optical signal 810 that could go into a series of optical sensors 811 that could generally consist of pyrometers, photodiodes, spectrometers or cameras, but could specifically consist of a photodiode. Additionally, there could be a stationary sensor 809 that could be any optical sensor in general but that specifically be a pyrometer. Pyrometer 809 has a very narrow field of view and is specifically looking at a witness region 812 on the build area 803 and is making very precise and rapid thermal measurements at the witness area 812. The data from the stationary pyrometer 809 is correlated to the data from the stationary photodiodes 805 and 807 as well as the in-line photodiode 811 in the event that the process is a laser based process. Additionally, there is an optical sensor 813 with a very large field of view 814 which encompasses the entire build area 803. This sensor 813 specifically could be a camera, either high speed or low speed, visible, UV, or IR, or a camera with a very large pixel density and therefore high spatial resolution. Even more specifically this camera could take pictures of the object being built layer by layer after every layer is deposited, and then could utilize this data to create a representation of the as-built part geometry by superimposing and concatenating or otherwise combining the individual 2-dimensional pictures into a fully 3-dimensional representation of the part and the as-built part geometry. In some embodiments, this configuration can be extended so that there are multiple photodiodes in addition to 805 and 807: as shown two photodiodes or other sensors distributed 180 degrees apart; three photodiodes or other sensors distributed 120 degrees apart, four photodiodes or other sensors distributed 90 degrees apart, etc. Also the pyrometer 809 could have a scanning capability which in the case of an electron beam based process would allow it to follow the beam 801 as it moves across the build area 803. This is also possible in the case that the energy source 800 is a laser.

Figure 9:
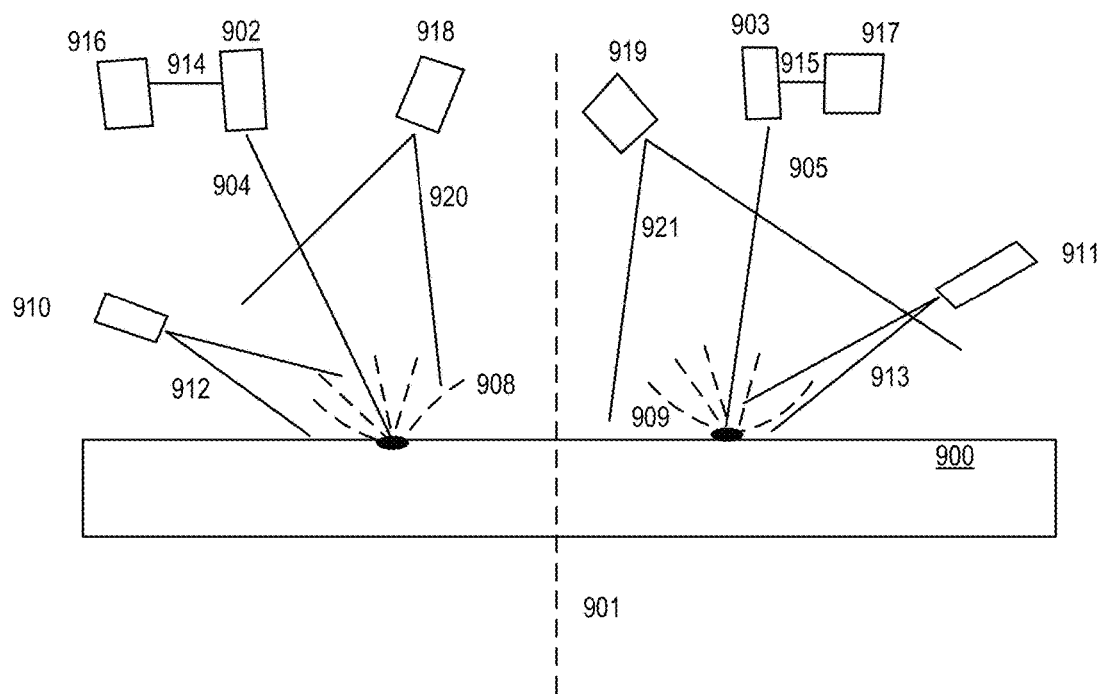

To increase the productivity of an additive manufacturing process, it may be desirable to have multiple heat sources. One possible configuration is shown in FIG. 9. In FIG. 9 the workpieces or total build area 900 is divided along a plane of symmetry 901. The operations to either side of 901 could be viewed as occurring completely independently. Of course some embodiments have some overlap across 901 in the event that the part being built on the build area 900 is a large, single part. Alternatively, there could be many smaller parts that are being built on the build area 900 and there might be no cross talk or communication across this symmetry plane 901 required whatsoever. In either event, the two heat sources 902 and 903 project finely focused and deflected beams 904 and 905 which create hot beam material interaction regions 906 and 907. Optical emissions, 908 and 909 from the regions 906 and 907 respectively can be collected by a series of sensors. In the embodiment illustrated in FIG. 9, it is shown that two sets of identical sensors act independently in each region of the build area 900 separated by the symmetry plane 901. However this is not a requirement and sensors could see all regions of the build area 900 as well. Stationary optical sensors 910 and 911 interrogate the hot regions 906 and 907. They have associated fields of view 912 and 913 which could be local or could encompass the entire area of the build 900. Additionally, in the event that the heat sources 902 and 903 are lasers, there is the potential to collect additional sensor data 914 and 915 through the laser scanning systems and these signals could then be measured by in-line sensors 916 and 917. Lastly there are two stationary sensors 918 and 919 which have fields of view 920 and 921 which cover at least their respective portions of the build area 900 as separated by the symmetry plane 901. These sensors 918 and 919 could for example be cameras which are measuring the as-built geometry in the two regions of the build area 900 divided by the symmetry plane 901. It is also noted that one extension of this concept is that the symmetry plane 901 could be just a simple diving plane, i.e. the areas to the left and to the right of 901 need not be equal. Also this concept is extensible to situations where there could be N heat sources acting on M different overlapping or separate regions. The sensors could have overlapping or separate fields of view. This concept can be extended, for example, to include:

- N heat sources acting on M areas, i.e. there need not be a one to one correspondence between heat sources and separate build areas
- Situations in which the multiple heat sources are generated from the same single beam. For example in electron beam additive manufacturing, it is possible to electromagnetically move the beam so fast that it effectively forms two or more heat sources on the workpiece area 900 by virtue of the fact that it spends a given amount of dwell time at each heat source location, and if the scan frequency is fast enough the beam can move from hot region to hot region without extinguishing the melt pool in between these transitions and jumps
- P stationary sensors like 910 and 911 that interrogate any of the M build areas, i.e. any combination of the (1, 2, . . . , M) areas interrogated by (1, 2, . . . , P) stationary sensors
- Q stationary sensors like 918 and 919 that interrogate any part of the M build areas, i.e. any combination of the (1, 2, . . . , M) areas interrogated by (1, 2, . . . ,Q) stationary sensors. Furthermore since the Q sensors of type 918 and 919 could be used to create in-process geometric measurements of as-built part geometry, these Q sensors acting over M areas could be combined in many ways to produce the overall geometry of the all the parts or part being built in the build area 900.

Irrespective of the sensor configurations and irrespective of whether or not there are multiple or single heat sources or energy beams, all of the in-process raw data can be processed such that features could be extracted from this raw data. The table below outlines the possible categories of feature extraction methods and techniques. The overall purpose of a feature extraction method is to reduce the size or dimensionality of a time-based raw data set by assigning features represent key physical characteristics and attributes of the original signal but by using reduced order representations.

a powder bed either with a laser or an electron beam, there are specific patterns. For example in FIG. 10, we see several different hatch patterns for a laser based process. In 1000, a region of the build area is processed by the laser beam scanning along very long path lengths that alternate in direction. In 1001, this same area is broken into smaller checkerboards which are scanned sequentially left to right and top to bottom. In 1002 the same checkboard pattern is shown, but now the scan order for the individual checkerboards is randomized. Irrespective of the specific scanning pattern or scanning strategy involved, it is seen that the laser based process involves short, many short, discrete scan lengths with a start and a stop and a path length.

If such a process were being monitored by a stationary photodiode, the data coming back to the photodiode would have many, many individual signals each representing a given specific scan over a specific path length. It would be useful to separate out all of these signals according to their path length, as the apparent intensity of the signal as observed by the photodiode will be a function of this path length. This is because at the start of the scan, the photodiode intensity is zero or very small because the laser has just turned on. As the scan proceeds the scan generally becomes hotter and emits more light, so the photodiode intensity would increase slightly. There would of course be a natural range and scatter in the photodiode raw signal as the light intensity varies throughout the process due to the very chaotic nature of the laser/powder interactions as well as the chaotic motion of the molten metal and the changing view factor from this small hot spot to the photodiode.

Figure 11:
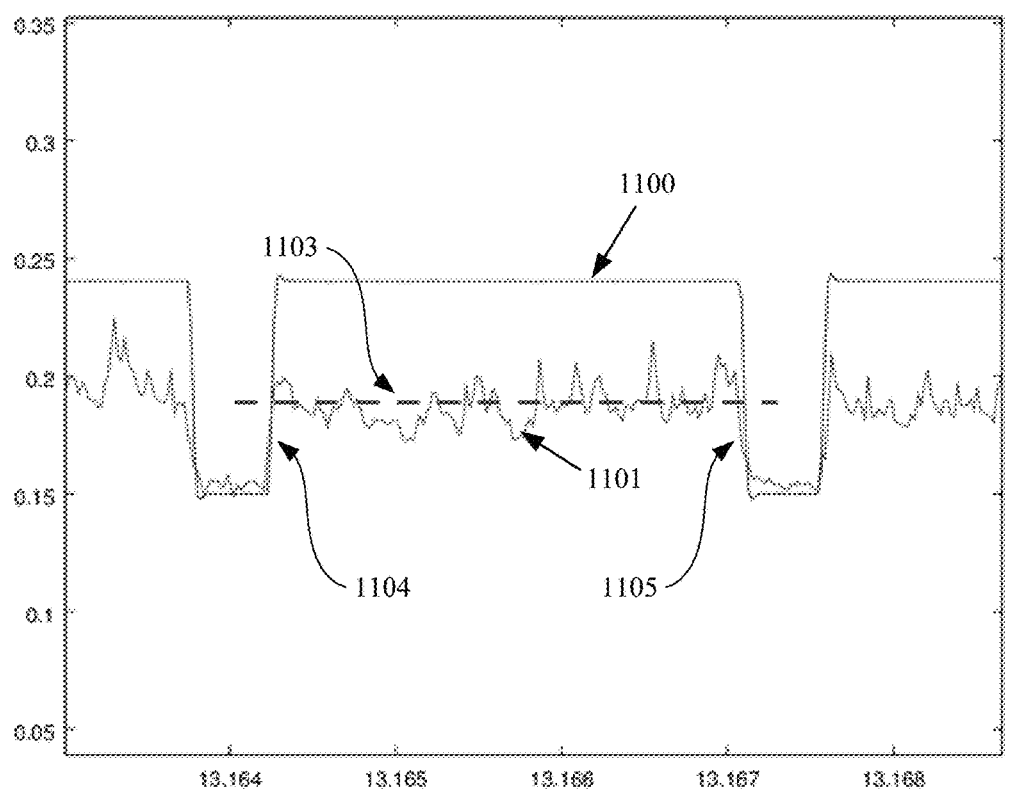

FIG. 11 shows a raw photodiode signal for a given scan length. 1100 is the laser drive signal, or the command signal which tells the laser to turn on and off for a specific scan length. The signal 1101 is the photodiode raw voltage superimposed over the laser drive signal. The rise and fall of 1101 can be clearly seen as well as the scatter and variation in the signal during the time that the laser is on. The data is collected a given number of samples per second. 1103 is a line representing the average signal value during the time that the laser was on for that specific scan length. The

| CATEGORY | EXAMPLES AND DESCRIPTION |
|---|---|
| Time based methods | These are techniques that look at the attributes of a signal as a function of time or over time. Simple control limits are examples, as are moving averages, other statistical moment functions acting directly on time-based data, or a many possible feature descriptors which could describe the envelope of the signal intensity vs. time curve |
| Frequency based methods | These involve the mathematical transformation of time-based data into a frequency domain using such transformation techniques as the Fourier Transform or numerical variants of that such as the Fast Fourier Transform or FFT. The essential premise here is that time based data could be represented as a summation of different sinusoidal or otherwise oscillatory signals with different weighting factors. |
| Time-frequency methods | Examples of these methods are the broad category of Wavelet transforms. The fundamental premise of these techniques is to examine the frequency content of a signal as it evolves over time. Q |
| Heuristic methods | Various figures of merit, dimensionless numbers, or any other manner of analysis that could result in sets of features that are reduced order and that represent the original time-based signal in some alternate space. |
| Other | Hybrid or ad hoc techniques which could be very specific to the manufacturing process in question. |

As an example of this last category of feature extraction methods, consider the following case which is specific to additive manufacturing and its unique peculiarities. In additive manufacturing that involves a scanning heat source on a powder bed either with a laser or an electron beam, there variation in 1101 can be caused by variations in powder being melted on the powder bed. For example, one of the minor troughs of 1101 can be caused by energy being absorbed by a larger particle in the particle bed transitioning from a solid state to a liquid state. In general, the number of data points in a given segment of the photodiode signal between rise and fall events can be related to the scan duration and the sampling rate. Furthermore, if the scan velocity of the laser is known, then the scan length can be similarly related to the number of points in a given photodiode segment between a rise and fall of the signal by the following relationship:

$$\text{(number of points in a given photodiode segment)} = \text{(sampling rate in Hz)} \cdot \frac{\text{(scan length in mm)}}{\text{(scan velocity in mm/s)}} \quad (13)$$

So it is seen that the number of data points in a given segment of photodiode data between a rise and fall event (i.e. time laser was on for a scan) is directly proportional to the scan length. It is possible therefore to plot all the photodiode data for all scan segments in the build as a function of the scan length, or correspondingly as a function of the number of data points in a given photodiode segment representing the data collected during a specific scan. In practice, there are not an infinite number of scan lengths used, and the same scan length may be used at many different locations in the part. Smaller scan lengths may be used for smaller geometrical features, and for larger features a larger scan length may be possible to speed up the build process. Embodiments of the present invention are, therefore, scan strategy agnostic. In other words, the effect of scan length is accounted for by the measurement of the number of data points collected. Machine to machine variations in scan strategy can be addressed using embodiments of the present invention since the scan length associated with each scan strategy is accounted for by the conversion to the number of samples in a scan illustrated in FIG. 12. Typically, the scan strategy is not accessible to the user. The system described herein thus enables machine to machine comparisons based on the measured data.

Figure 12:
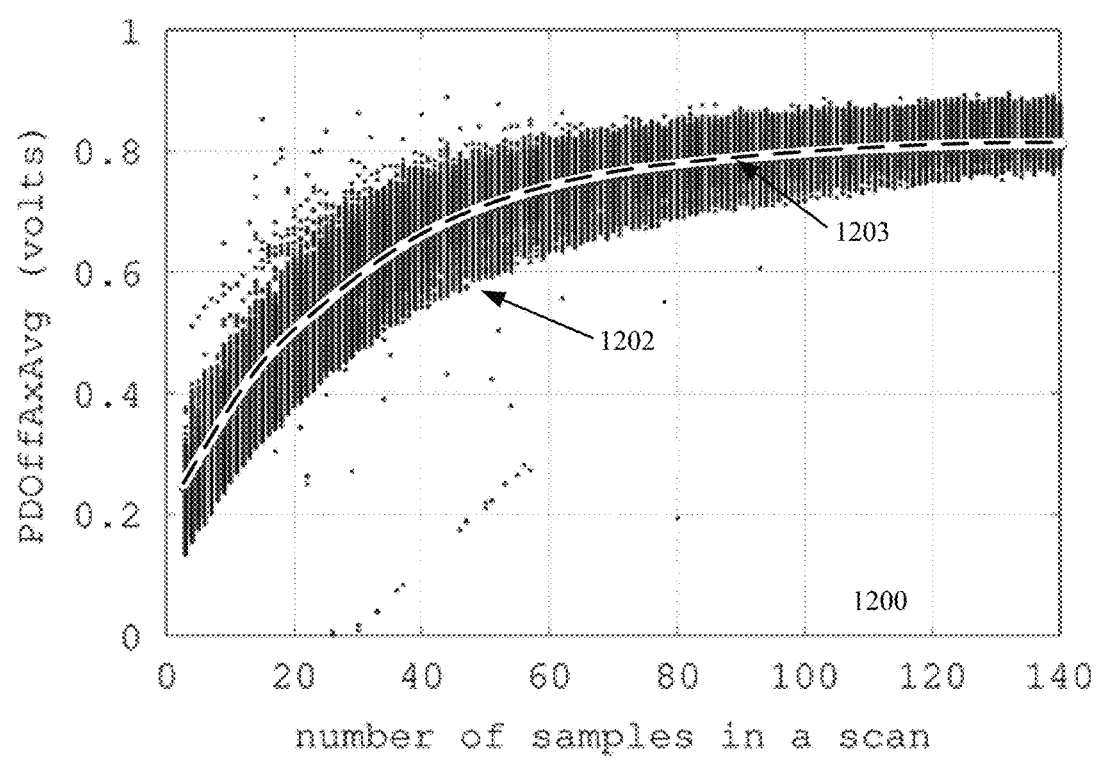

FIG. 12 shows the result of plotting the photodiode data in this manner, namely the raw photodiode voltage signal as a function of the number of data points in the individual sample. Also, the average of the data for a given length has been taken. This would correspond to 1103 in FIG. 11 as discussed above. In other words, each data point in FIG. 13 represents an average over the small segment of photodiode data corresponding to a specific scan. Along the abscissa of FIG. 12 is the number of samples or data points in a given scan 1200. Along the ordinate of FIG. 12 is the average raw photodiode voltage value for that corresponding scan length 1201. Each individual point again is the average for a given scan. The entire body of point clouds of such average data 1202 is not random but does exhibit a distinct order and has a characteristic shape. This point cloud shape 1202 can be fitted with a best-fit line 1203. This line 1203 is a FEATURE which is very useful for characterizing this process condition since 1203 is unique to the process inputs and the scan strategy. Therefore it is a feature extraction technique that can define processes as equivalent (e.g., machine to machine) if the same best-fit line 1203 is produced. Using the line 1203 from a first machine, the process input settings and scan strategy (which can both be different) for a second machine can be modified until the same line 1203 is produced (within predetermined tolerances), indicating that the process outcome is the same for both machines. The technique is summarized below.

Figure 10:
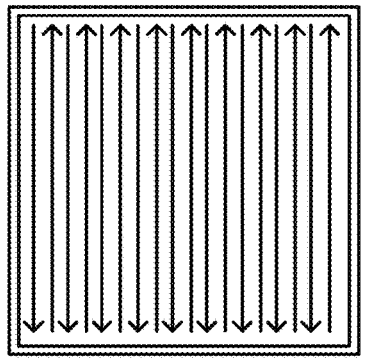
FIGS. 10-12 show scan patterns and graphs related to accounting for scan pattern variations using measurements from an optical sensor.
Figure 10:
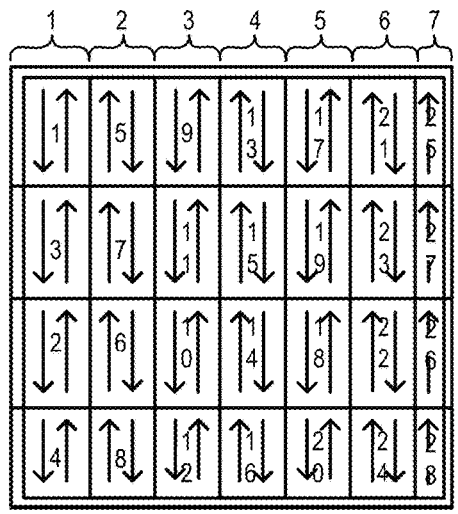
Figure 10:
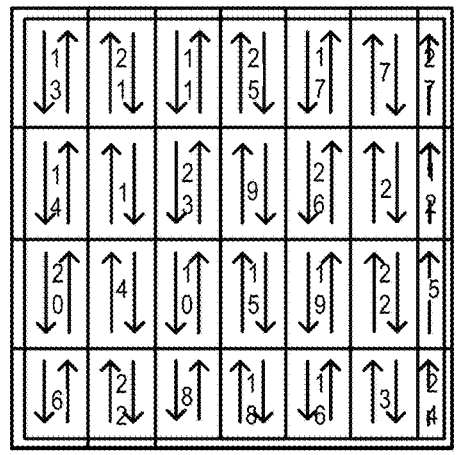

1) GIVEN a beam power, a beam travel speed, and all other process conditions and inputs fixed
2) GIVEN a scan strategy for a particular component (e.g. scan strategy as illustrated in FIG. 10), i.e. a distribution of scan lengths
3) THEN perform the following steps to derive this process feature:
   a. Identify the rise and fall for each segment of photodiode data, i.e. the region in time over which the laser was on and the photodiode was collecting data.
   b. Count the number of points in this data sample
   c. Calculate the average photodiode intensity over this time segment, i.e. take the numerical average of the raw photodiode data between the rise and fall of the signal, i.e. over which time the laser was actually on
   d. Plot this average as a function of the number of points in the sample
   e. Repeat this process for a given number of scans, which could be just the scans on a given layer, or could include multiple layers, or could even be for an entire part, or could be for multiple parts in a given build, or could be for multiple builds over an extended period of time.
   f. Put a best fit curve through the center of the resultant data cloud
   g. This best fit curve is now a process feature derived from raw stationary photodiode data that is characteristic of a given operating condition—i.e. all process inputs fixed, and is also characteristic of a given scan strategy
   h. When the process inputs or scan strategy changes, this curve will change and therefore changes in this curve are reflective and predictive of changes in the underlying processing conditions for the additive manufacturing process in question Lastly is should be observed that there is no fundamental reason why this technique cannot be applied to processes that utilize electron beam heat sources, provided that they also employ scan strategies in which smaller regions of the build are scanned by a large number of short individual scan paths.

Referring once again to FIG. 11, the slope of the photodetector response line 1101 can be measured when the laser is turned off, represented by 1100. As illustrated in FIG. 11, the slope of 1101 when the laser turns off is less than the slope of 1101 when the laser turns on. These differing slopes are evident in FIG. 11 at about 13.164 to 13.1643 (1104). Similar behavior is illustrated at 13.1672 to 13.1677 (1105). The lower slope 1105 associated with 1101 when the laser turns off corresponds to the metallurgical cooling rate of the material. The higher slope associated with 1101 when the laser turns on corresponds to the metallurgical heating rate of the powders. Accordingly, the systems described herein provide insight into these cooling and heating rates not available using conventional techniques.

Measurements of heating rates and cooling rates as a function of 3D position in the manufactured part can be made and utilized to determine the microstructure of the material during each of the scan lines. Thus, the heating and cooling rates at each 3D location in the build can be determined using embodiments of the present invention, which are not available using conventional techniques. As a result, using a stationary photodiode in some embodiments, a 3D map of heating and cooling rates can be compiled and then correlated with in-process and post-process material characterization data. Referring to FIG. 9, the measurements of heating and cooling rates can be used to baseline operation on the illustrated two different portions of the build plane.

Figures 13A, 13B:
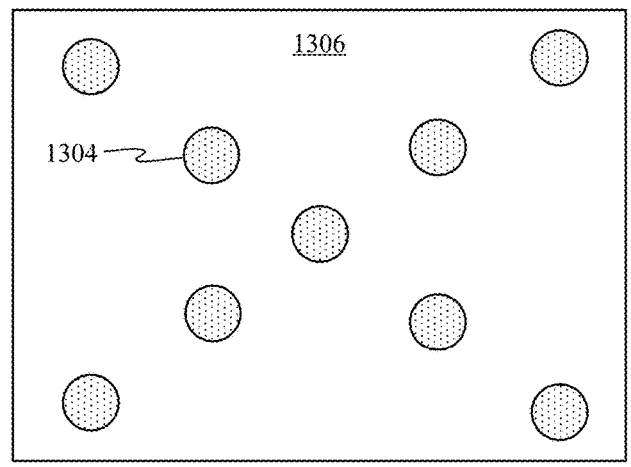
FIG. 13A shows a chart that includes machine settings suitable for use with a test pattern.
FIG. 13B shows a test pattern suitable for use with the machine settings of FIG. 13A.

FIG. 13A illustrates a set of machine settings 1300 suitable for testing the performance of an additive manufacturing device. In particular, the power of the laser emitted by the additive manufacturing device is varied from 55% below nominal to 45% above nominal power levels. This variation in power level can be used to evaluate the performance of the additive manufacturing device across a large range of operating conditions. The leftmost column shows which layers corresponding to each set of machine settings. Machine settings 1300 indicate that the laser travels across the build plane at a constant speed of 1200 mm/s, a length of each laser actuation is held constant at 0.09 mm and GED or energy density varies as a function of the varying laser power.

FIG. 13B shows a top view of a test pattern 1302 that can be used with machine settings 1300 depicted in FIG. 13A. Test pattern 1302 can include a number of circular cylinders 1304 distributed across build plane 1306. While a similar configuration was used when carrying out test runs in accordance with the machine settings of FIG. 13A other test patterns are also possible. For example, a width of circular cylinders 1304 can be varied over the course of a build. Furthermore, various features could protrude radially from cylinders 1304 in order to more fully test the performance of the additive manufacturing device building parts with substantial geometric variations.

Figure 14A:
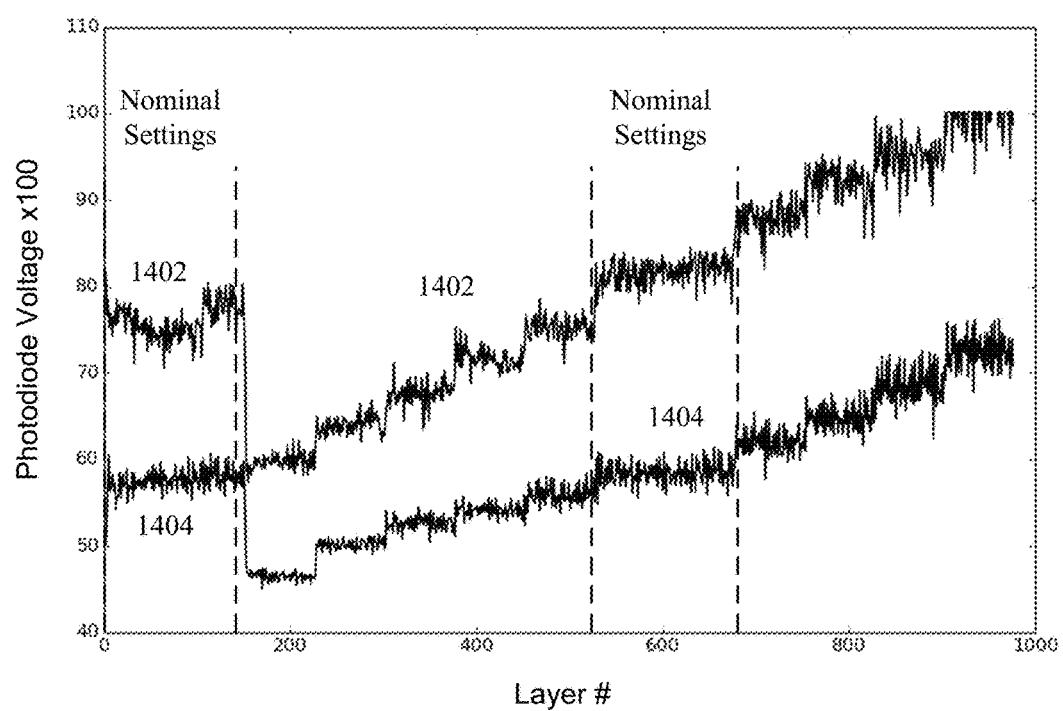
FIGS. 14A-14F show various graphs illustrating features extracted from sensors monitoring an additive manufacturing operation using the machine settings of FIG. 13A and the test pattern of FIG. 13B.

FIGS. 14A-14F show various graphs illustrating features extracted from sensors monitoring an additive manufacturing operation using the machine settings of FIG. 13A and the test pattern of FIG. 13B. In particular, FIG. 14A shows sensor readings averaged over the build plane from two different sensors monitoring build plane 1306 using machine settings 1300 depicted in FIG. 13A. In particular, line 1402 represents the intensity in volts measured by a photodiode positioned similarly to sensor 609 of FIG. 6 while monitoring build plane 1306. In this way, the photodiode output represented by line 1402 can be referred to as an on-axis measurement. The term on-axis refers to the sensor sharing the same optical path as the heat source, allowing the sensor to be focused narrowly on the location undergoing heating. Line 1404 is associated with a photodiode positioned similarly to sensor 610 of FIG. 6. The measurements taken by this photodiode can be referred to as off-axis measurements since the readings are typically recorded from one side of build plane 1306 and include the entire build plane 1306. Because line 1404 represents readings collected by a sensor having a field of view encompasses all of build plane 1306, the raw sensor readings tend to be lower than the sensor readings generating line 1402. The sensor readings represented by lines 1402 and 1404 show that both photodiodes are capable of distinguishing between the different laser power levels utilized over the course of the performance test. In particular, the dashed lines indicate which portion of the graph utilizes nominal laser settings. While there is some variation between the intensities measured for layers 0-150 and 525-675, the numbers are generally closer to each other than to any of the other segments of the build that use different settings. In some cases, the slight differences can be accounted for by heating of the build plane over the duration of the build.

Figure 14B:
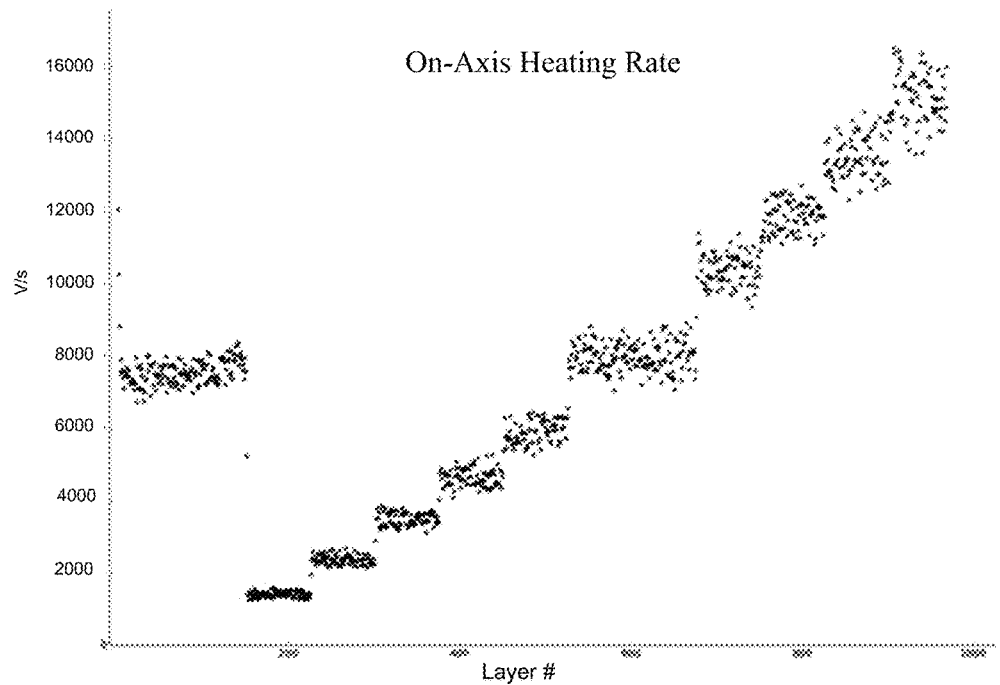
Figure 14C:
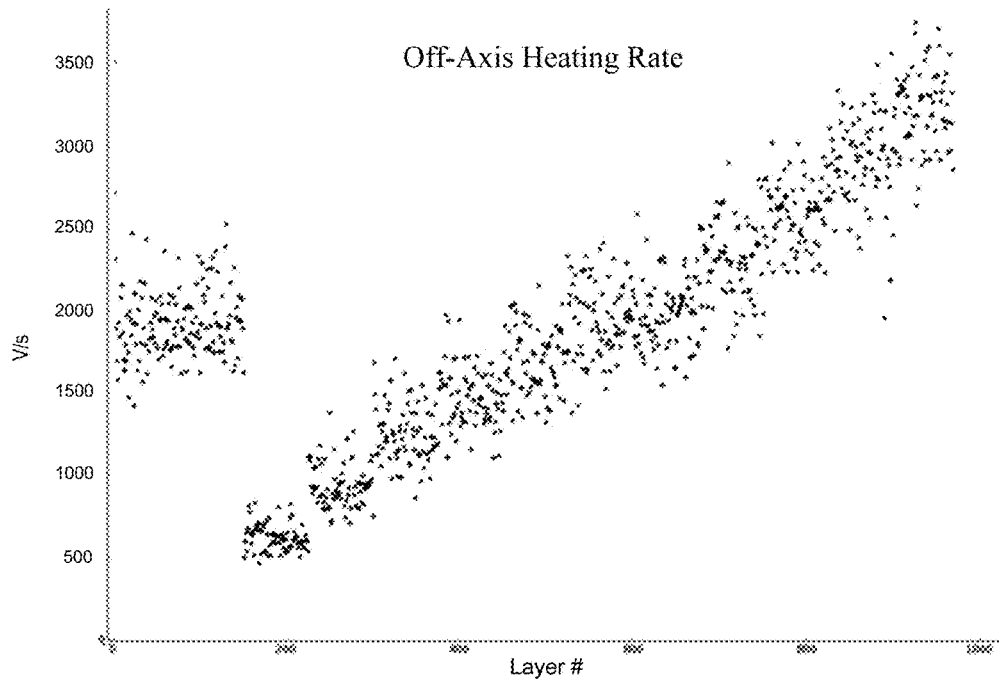

FIGS. 14B-14C show heating rates calculated using on-axis and off-axis raw sensor data associated with laser actuations made during a test build and recorded concurrently by two different photodiodes. The heating rates are calculated from data associated with portion 1104 of curve 1101 as shown in FIG. 11. FIGS. 14B and 14C both demonstrate how both the on-axis and off-axis photodiodes are able to show clear heating rate differences corresponding to the different laser power output.

Figure 14D:
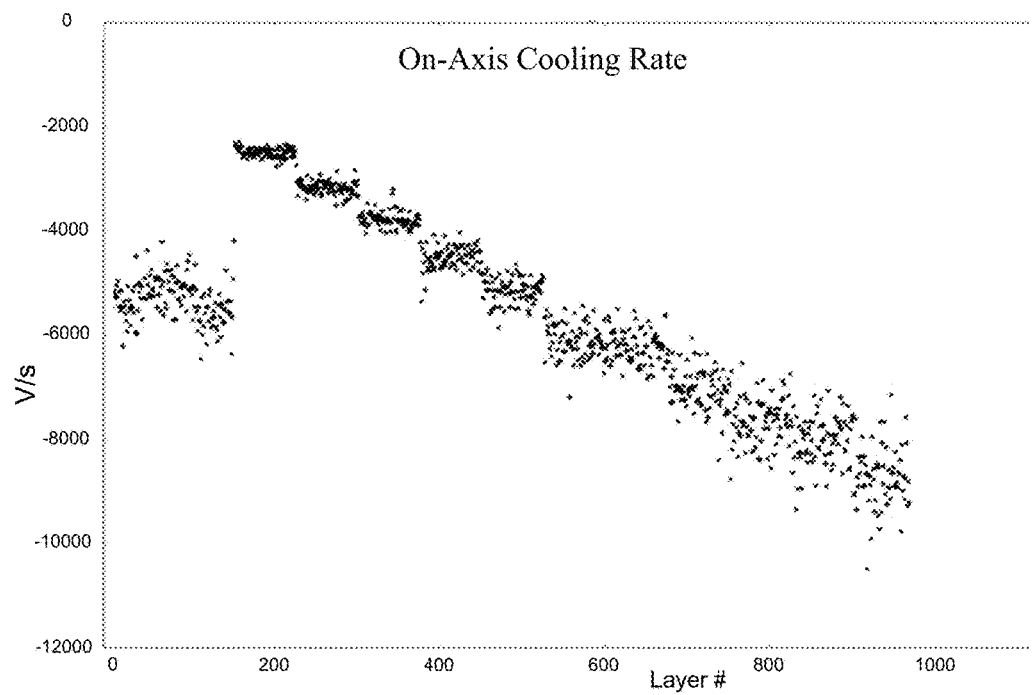
Figure 14E:
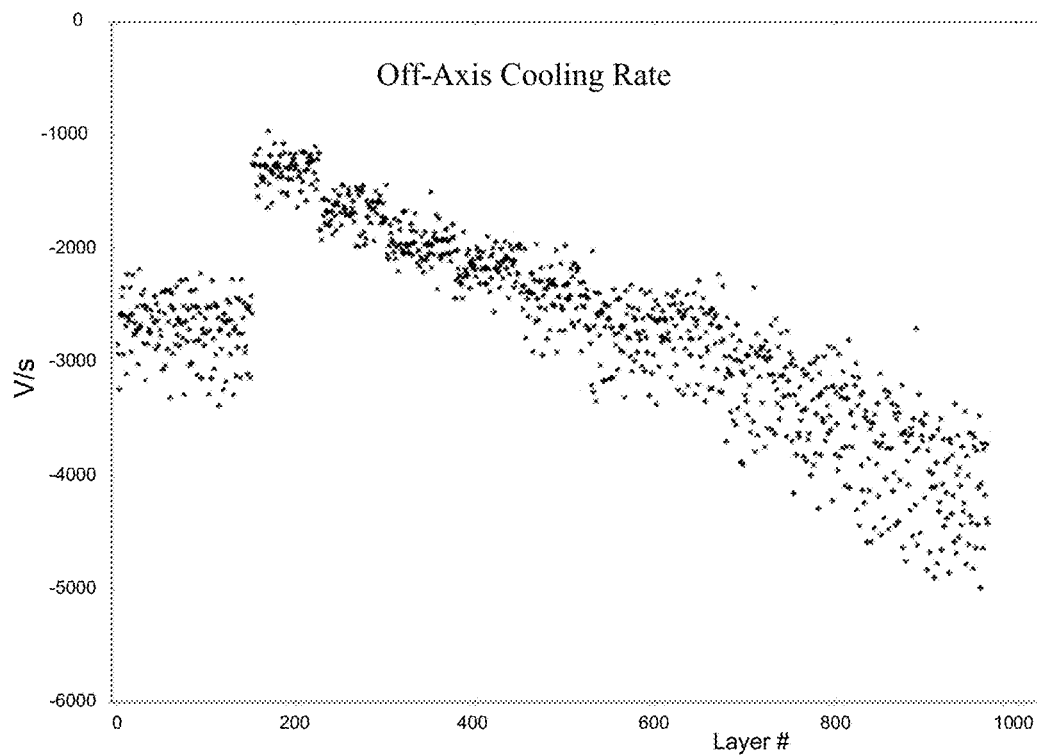

FIGS. 14D-14E show cooling rates calculated using on-axis and off-axis sensor data associated with laser actuations made during a test build using machine settings 1300 and recorded concurrently by two different photodiodes. The cooling rates are calculated from sensor data corresponding to portion 1105 of curve 1101 as shown in FIG. 11. FIGS. 14D and 14E both demonstrate how both the on-axis and off-axis photodiodes are able to show differences in cooling rates that correspond to the different laser power outputs. Differences in cooling rates between FIGS. 14D and 14E can be caused by the smaller signal intensity received by the off-axis photodiode used to collect the data displayed by FIG. 14E. Other factors that could be considered as part of a calibration process include analysis of peak power and an amount of deviation experienced using each different setting.

Figure 14F:
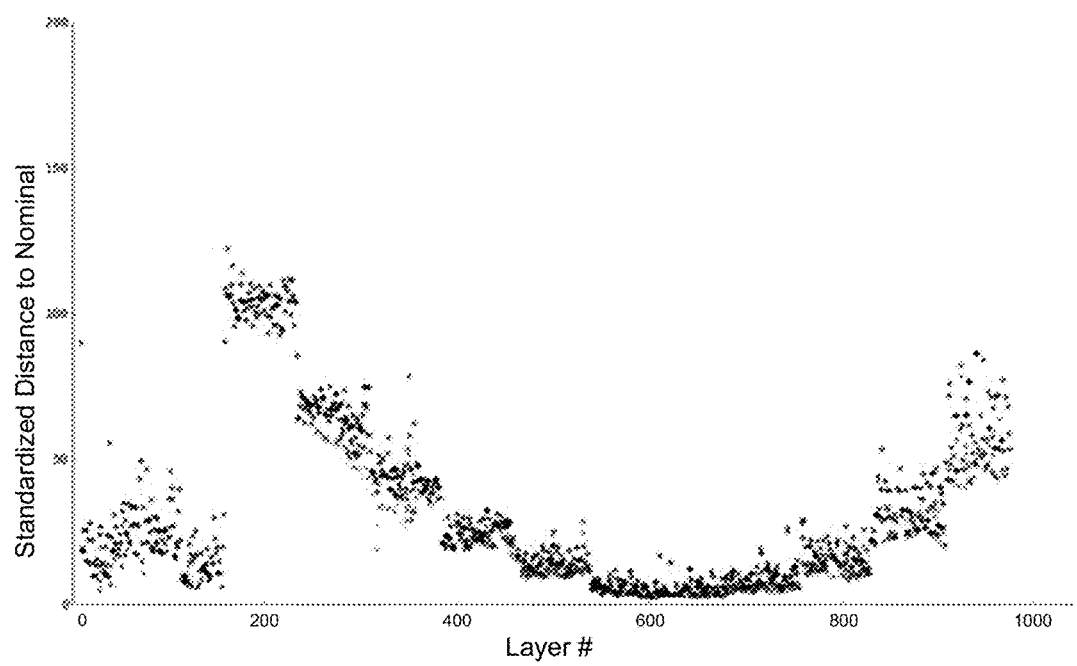

FIG. 14F shows a graph in which heating rate and cooling rate data is combined. The data is combined to more clearly identify variations in laser power. In FIG. 14F, the heating and cooling rate data depicted in FIGS. 14B-14E have been standardized using sensor data collected while nominal laser settings are used in building layers 525-675. In particular, the data can be standardized using a multivariate classifier such as a Mahalanobis Distance calculation, which indicates how many standard deviations each heating or cooling rate is from a nominal distribution of heating/cooling rates. In this case, the Mahalanobis Distance indicates how many standard deviations away the combined cooling rate and heating rate is from the mean heating rate or cooling rate collected while building layers 525-675. The combined and standardized heating and cooling rate data shows variation as a function of laser power as depicted in FIG. 14F. In some embodiments, the performance of the additive manufacturing device can be further verified by comparing quantitative metallographic features (e.g. the size and shape of pores or intermetallic particles) and/or mechanical property features (e.g. strength, toughness or fatigue) of the metal parts created while performing the test runs. In general, the presence of unfused metal powder particles in the test parts indicates not enough energy was applied while test parts that received too much energy tend to develop internal cavities that can both compromise the integrity of the created part.

In some embodiments, a nominal value used to generate FIG. 14F will be taken from a preceding test. In some embodiments, the nominal value could also be taken from a subsequent test since the calculations do not need to be done during the additive manufacturing operation. For example, when attempting to compare performance of two additive manufacturing devices, a nominal value can be identified by running a test using a first one of the additive manufacturing devices. The performance of the second additive manufacturing device could then be compared to the nominal values defined by the first additive manufacturing device. In some embodiments, where performance of the two additive manufacturing devices is within a predetermined threshold of five standard deviations comparable performance can be expected from the two machines. In some embodiments, the predetermined threshold can be a 95% statistical confidence level derived from an inverse chi squared distribution. This type of test methodology can also be utilized in identifying performance changes over time. For example, after calibrating a machine results of a test pattern can be recorded. After a certain number of manufacturing operations are performed by the device, the additive manufacturing device can be performed again. The initial test pattern performed right after calibration can be used as a baseline to identify any changes in the performance of the additive manufacturing device over time. In some embodiments, settings of the additive manufacturing device can be adjusted to bring the additive manufacturing device back to its post-calibration performance.

Using a test pattern, such as the test pattern depicted in FIG. 13B, that is distributed across the build plane allows the various regions of an additive manufacturing device to all be tested. Furthermore, while the exemplary changes in settings were limited to laser power, other settings such as laser speed and hatch pattern pitch could also be modulated to change the power density applied to each portion of the test pattern. Consequently, numerous features process parameters of a given additive manufacturing device can be characterized by comparing performance of various test patterns. In some embodiments, the test pattern can take the form of a commercial part and various changes in machine settings can be correlated with different features of the commercial part. For example, this type of testing methodology could be used to characterize how a part's structural integrity changed as a function of a particular laser power. This type of testing that involves calibrating for a specific part could be helpful where the additive manufacturing device is used to create a limited number of different parts.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A method for calibrating an additive manufacturing device, the method comprising:
    monitoring photons emitted as energy impacts metal powder spread across a build plane during a first additive manufacturing operation performed by a first additive manufacturing device, the monitoring being performed using one or more optical sensors;
    recording sensor data captured by the one or more optical sensors;
    identifying one or more actuations of a heat source of the first additive manufacturing device using changes in intensity from the recorded sensor data;
    counting a number of actuations of the heat source;
    calculating a first best fit curve over time based on the changes in intensity and counted number of actuations;
    comparing the first best fit curve to a second best fit curve based on sensor data collected during a second additive manufacturing operation performed by a second additive manufacturing device;
    determining differences between the first and second best fit curves; and
    calibrating the second additive manufacturing device using the determined differences.

2. The method as recited in claim 1, wherein at least one optical sensor of the one or more optical sensors is a photon to electrical signal transducer.

3. The method as recited in claim 1, further comprising:
    extracting a heating rate, cooling rate and average intensity associated with energy impacting the metal powder from the sensor data.

4. The method as recited in claim 3, wherein comparing the first and second best fit curves comprises determining whether or not the second best fit curve falls within a predetermined threshold range of the first best fit curve.

5. The method as recited in claim 4, wherein the predetermined threshold range is a 95% statistical confidence level.

6. The method as recited in claim 1, wherein the first additive manufacturing device is different than the second additive manufacturing device.

7. The method as recited in claim 1, wherein the additive manufacturing operations comprise a test pattern.

8. The method as recited in claim 7, wherein an intensity of the emitted photons varies over the course of the test pattern.

9. The method as recited in claim 1, further comprising:
    comparing an internal grain structure of parts produced by both the first and second additive manufacturing operations to verify the calibration of the second additive manufacturing device.

10. The method as recited in claim 1, wherein the one or more optical sensors comprises an off-axis photodiode and an on-axis photodiode.

11. A method for an additive manufacturing device, comprising:
    conducting an additive manufacturing operation to build a test part during which operating parameters of the additive manufacturing device are varied;
    absorbing photons emitted from a build plane of the additive manufacturing device using a photodiode;
    extracting features from variations in a number of photons absorbed by the photodiode, extracting features comprising:
        identifying one or more actuations of a heat source of the additive manufacturing device using changes in intensity recorded by the photodiode;
        counting a number of actuations of the heat source; and
        calculating a best fit curve over time for the number of actuations; and
    comparing the extracted features to baseline features.

12. The method as recited in claim 11, wherein the baseline features are extracted by carrying out the same additive manufacturing operation on another additive manufacturing device.

13. The method as recited in claim 11, wherein the photodiode and the heat source of the additive manufacturing device use the same optical path.

14. The method as recited in claim 11, wherein the extracted features are selected from a group consisting of an average heat source intensity, a peak temperature, a cooling rate and a heating rate.

15. The method as recited in claim 11, wherein a pyrometer with a field of view covering a portion of the build plane is also used to monitor heat emitted from the build plane.

16. The method as recited in claim 11, wherein the baseline features were extracted by carrying out the same additive manufacturing operation on the same additive manufacturing device at an earlier time.

17. A calibration system configured to measure performance of an additive manufacturing device having a heat source and a build plane, the calibration system comprising:
an optical sensor suite configured to absorb photons emitted from the build plane during an additive manufacturing operation;
a data storage device configured to store readings taken by the optical sensor suite; and
a processor configured to:
extract features from the stored readings by identifying one or more actuations of the heat source of the additive manufacturing device using changes in intensity recorded by the optical sensor suite, counting a number of actuations of the heat source, and calculating a best fit curve over time for the counted number of actuations;
compare the extracted features to a set of baseline features associated with another additive manufacturing device or with the same additive manufacturing device.

18. The calibration system as recited in claim 17, wherein the optical sensor suite comprises an off-axis photodiode and an on-axis photodiode.

19. The calibration system as recited in claim 17, wherein data associated with the extracted features is combined and standardized to characterize the performance of the additive manufacturing device.

20. The calibration system as recited in claim 17, wherein the processor is further configured to generate updated operating parameters for the additive manufacturing device.

* * * * *